United States Patent [19]
Greenberg et al.

[11] Patent Number: 5,470,730
[45] Date of Patent: Nov. 28, 1995

[54] METHOD FOR PRODUCING $T_H$-INDEPENDENT CYTOTOXIC T LYMPHOCYTES

[75] Inventors: Phillip D. Greenberg, Mercer Island; Robert W. Overell, Seattle, both of Wash.

[73] Assignees: Immunex; Fred Hutchinson Cancer Research Center, both of Seattle, Wash.

[21] Appl. No.: 287,111

[22] Filed: Aug. 8, 1994

Related U.S. Application Data

[63] Continuation of Ser. No. 55,903, Apr. 29, 1993, abandoned, which is a continuation of Ser. No. 764,596, Sep. 24, 1991, abandoned, which is a continuation-in-part of Ser. No. 614,167, Nov. 9, 1990, abandoned, which is a continuation-in-part of Ser. No. 589,939, Sep. 28, 1990, abandoned.

[51] Int. Cl.$^6$ .............................. C12N 15/12; C12N 5/10
[52] U.S. Cl. .................. 435/172.3; 435/69.1; 435/69.52; 435/70.4; 435/252.3; 435/326.1; 424/93.21
[58] Field of Search ................................ 435/69.1, 69.52, 435/70.4, 172.3, 320.1; 432/882.3; 424/93 B

[56] References Cited

U.S. PATENT DOCUMENTS 5,272,082  12/1993  Santoli et al. ..................... 435/240.2

FOREIGN PATENT DOCUMENTS 0318296  5/1989  European Pat. Off. .
0460846  12/1991  European Pat. Off. .

OTHER PUBLICATIONS

Karasuyama et al, *J. Exp. Med.* 169, 1989, pp. 13–25.
Ullman et al, *Annu. Rev. Immunol*, 8, 1990, pp. 421–452.
Bodine et al, *New York Academy Sci* 612, 1990, pp. 415–426.
Starking et al *Cell* 53, 1988, pp. 869–879.
Curtis et al, *P.N.A.S.* 86:3045–3049, May 1989.
World Patent Index (WPI) Database abstract of Patent Publication No. AU–4615089 (Jun. 21, 1990), Derwent Publications, Ltd., London, GB, 1 page total.
Mukherji, B. et al., "T–cell clones that react against autologous human tumors" *Immunol. Rev.* (1990) 116:33–62.
Sims et al., "cDNA Expression Cloning of the IL–1 Receptor, a Member of the Immunoglobulin Superfamily" *Science* 241:585 (Jul. 29, 1988).
Nishihara et al., "Augmentation of Tumor Targeting in a Line of Gliona-specific Mouse Cytotoxic T–Lymphocytes by Retroviral Expression of Mouse γ–Interferon Complementary DNA$^1$" *Cancer Research* 48:4730 (Sep. 1, 1988).
Plate et al., "Cytokines Involved in the Generation of Cytolytic Effector T Lymphocytes$^\alpha$" *Annals New York Academy of Sciences* 532:149 (1988).
Fitch et al., "Regulation of T Lymphocyte Responses: Interactions among Receptors" *Immune System and Cancer*, T. Hamaoka et al. (Eds.), pp. 15–27 (1989).
Rosenberg, Adoptive Immunotherapy for Cancer, *Scientific American*, pp. 62–69, (May, 1990).

Klarnet, et al., Antigen–Driven T Cell Clones Can Proliferate In Vivo, Eradicate Disseminated Leukiemia, And Provide Specific Immunologic Memory, *Journal of Immunology* 138:4012–4017, (Jun., 1987).
Sprent, et al., Properties of Purified T Cell Subsets, I. In Vitro Responses to Class I vs. Class II H–2 Alloantigens, *J. Exp. Med.* 162:2068–2066, (Dec., 1985).
Andrus, et al., Cytotoxic T Cells Both Produce And Respond To Interleukin 2, *J. Exp. Med.* 59:647–652, (Feb., 1984).
von Boehmer, et al., Lyt–2$^-$ T Cell–Independent Functions of Lyt–2$^+$ Cells Stimulated With Antigen Or Concanavalin A, *Journal of Immunology* 133:59–64.
Matis, et al., Adoptive Immunotherapy of a Syngeneic Murine Leukemia with a Tumor–Specific Cytotoxic T Cell Clone and Recombinant Human Interleukin 2: Correlation with Clonal IL2 Receptor Expression, *Journal of Immunology* 136:3496–3501, (May, 1986).
Mizuochi, et al., Role of Lymphokine–Secreting CD8+ T Cells in Cytotoxic T Lymphocyte Responses Against Vaccinia Virus, *Journal of Immunology* 142:270–273, (Jan., 1989).
Zinkernagel, et al., MHC–Restricted Cytotoxic T Cells: Studies on the Biological Role of Polymorphic Major Transplantation Antigens Determining T–Cell Restriction–Specificity, Function, and Responsiveness, *Advances in Immunology* 27:51–177, (1979).
Male, et al., Cytotoxic Lymphocytes, (*Advanced Immunology*, Chapter 7, Gower Publ., London; 1987).
Jacobson, et al., Measles Virus–Specific T4+ Human Cytotoxic T Cell Clones are Restricted by Class II HLA Antigens, *Journal of Immunology* 133:754–757, (Aug., 1984).
Gillis, et al., Long term culture of tumour–specific cytotoxic T cells, *Nature* 268:154–156, (Jul., 1977).
Cheever, et al., Augmentation of the Anti–Tumor Therapeutic Efficacy of Long–Term Cultred T Lymphocytes by In Vivo Administration of Purified Interleukin 2, *J. Exp. Med.* 155:968–980, (Apr. 1982).
Reddehase, et al., CD8–Positive T Lymphocytes Specific for Murine Cytomegalovirus Immediate–Early Antigens Mediate Protective Immunity, *Journal of Virology* 61:3102–3108, (Oct., 1987).
Rosenberg, et al., Use of Tumor–Infiltrating Lymphocytes and Interleukin–2 in the Immunology of Patients with Metastatic Melanoma, *N. Engl. J. Med.* 319:1676–1680, (Dec., 1988).
Klarnet, et al., Helper–Independent CD8+ Cytotoxic T Lymphocytes Express IL–1 Receptors and Require IL–1 for Secretion of IL–2, *Journal of Immunology* 142:2187–2191, (Apr., 1989).

(List continued on next page.)

Primary Examiner—Garnette D. Draper
Assistant Examiner—John D. Ulm
Attorney, Agent, or Firm—Morrison & Foerster

[57] ABSTRACT

The present invention relates to cytotoxic T lymphocytes (CTLs) which have been converted to a helper T cell independent phenotype by introducing a recombinant expression vector encoding IL-1 receptor into the CTL. The resulting CTLs have the ability to grow or function independent of T cell help.

13 Claims, 11 Drawing Sheets

OTHER PUBLICATIONS

Alderson, et al., Interleukin 7 Enhances Cytolytic T Lymphocyte Generation and Induces Lymphokine–activated Killer Cells from Human Peripheral Blood, *J. Exp. Med.* 172:577–587, (Aug. 1990).

Walker, et al., HIV–specific cytotoxic T lymphocytes in seropositive individuals, *Nature* 328:345–348, (Jul., 1987).

Plata, et al., AIDS virus–specific cytotoxic T lymphocytes in lung disorders, *Nature* 328:348–351, (Jul., 1987).

Siliciano, et al., Analysis of Host–Virus Interactions in AIDS with Anti–gp120 T Cell Clones: Effect of HIV Sequence Variation and a Mechanism for CD4+ Cell Depletion, *Cell* 54:561–575, (Aug., 1988).

Walker, et al., Long–term culture and fine specificity of human cytotoxic T–Lymphocyte clones reactive with human immunodeficiency virus type 1, *Proc. Natl. Acad. Sci. USA* 86:9514–9518, (Dec., 1989).

Chenciner, et al., Multiple subsets of HIV–specific cytotoxic T lymphocytes in humans and in mice, *Euro. J. Immunol.* 19:1537–1544, (1989).

Klarnet, et al., *Role of Interleukin–2 Activated Killer Cells in Cancer*, Lotzova and Herberman, eds, CRC Press; pp. 199–218, (1990).

Dower, et al., The interleukin–1 receptor, *Immunology Today* 8:46–51, (1987).

Bomsztyk, et al., Evidence for different interleukin 1 receptors in murine B– and T–cell lines, *Proc. Natl. Acad. Sci. USA* 86:8034–8038, (1989).

Lowenthal, et al., Expression of Interleukin 1 Receptors is Restricted to the L3T4+ Subset of Mature T Lymphocytes, *Journal of Immunology* 138:1–3, (1987).

Yamasaki, et al., Cloning and Expression of the Human Interleukin–6 (BSF–2/IFNβ 2) Receptor, *Science* 241:825–828, (1988).

Smith, et al., A Receptor for Tumor Necrosis Factor Defines an Unusual Family of Cellular and Viral Proteins, *Science* 248:1019–1023, (1990).

Loetscher, et al., Molecular Cloning and Expression of the Human 55 kd Tumor Necrosis Factor Receptor, *Cell* 61:351–359, (1990).

Schall, et al., Molecular Cloning and Expression of a Receptor for Human Tumor Necrosis Factor, *Cell* 61:361–370, (1990).

von Ruden, et al., Expression of functional human EGF receptor on murine bone marrow cells, *The EMBO Journal* 7:2749–2756, (1988).

Pierce, et al., Signal Transduction Through the EGF Receptor Transfected in IL–3–Dependent Hematopoietic Cells, *Science* 239:628–631, (1988).

Kurt–Jones, et al., Heterogeneity of Helper/Inducer T Lymphocytes, I. Lymphokine Production and Lymphokine Responsiveness, *Journal of Experimental Medicine* 166:1774–1787, (1987).

Greenbaum, et al., Autocrine Growth of CD4+ T Cells: Differential Effects of IL–1 on Helper and Inflammatory T Cells, *Journal of Immunology* 140:1555–1560, (1988).

Williams, et al., Introduction of new genetic material into pluripotent haematopoietic stem cells of the mouse, *Nature* 310:476–480, (1984).

Dick, et al., Introduction of a Selectable Gene into Primitive Stem Cells Capable of Long–Term Reconstitution of the Hematopoietic System of W/W$^v$ Mice, *Cell* 42:71–79, (1985).

Keller, et al., Expression of a foreign gene in myeloid and lymphoid cells derived from multipotent haematopoietic precursors, *Nature* 318:149–154, (1985).

Rosenberg, et al., Gene Transfer into Humans—Immunotherapy of Patients with Advanced Melanoma, Using Tumor–Infiltrating Lymphocytes Modified by Retroviral Gene Transduction, *New England Journal of Medicine* 323:570–578, (1990).

Miller, et al., Retrovirus Packaging Cells, *Human Gene Therapy* 1:5–14, (1990).

Kasid, et al., Human gene transfer: Characterization of human tumor–infiltrating lymphocytes as vehicles for retroviral–mediated gene transfer in man, *Proc. Natl. Acad. Sci. USA* 87:473–477, (1990).

Fearon, et al., Interleukin–2 Production by Tumor Cells Bypasses T Helper Function in the Generation of an Antitumor Response, *Cell* 60:397–403, (1990).

Russell, Lymphokine gene therapy for cancer, *Immunology Today* 11:196–200, (1990).

Sims et al., "cDNA Expression Cloning of the IL–1 Receptor, a Member of the Immunoglobulin Superfamily" *Science* 241:585 (Jul. 29, 1988).

Nishihara et al., "Augmentation of Tumor Targeting in a Line of Gliona–specific Mouse Cytotoxic T–Lymphocytes by Retroviral Expression of Mouse γ–Interferon Complementary DNA[1]" *Cancer Research* 48:4730 (Sep. 1, 1988).

Plate et al., "Cytokines Involved in the Generation of Cytolytic Effector T Lymphocytes[α]" *Annals New York Academy of Sciences* 532:149 (1988).

Fitch et al., "Regulation of T Lymphocyte Responses: Interactions among Receptors" Immune System and Cancer, T. Hamaoka et al. (Eds.), pp. 15–27 (1989).

Rosenberg, Adoptive Immunotherapy for Cancer, *Scientific American*, pp. 62–69, (May, 1990).

Klarnet, et al., Antigen–Driven T Cell Clones Can Proliferate In Vivo, Eradicate Disseminated Leukiemia, And Provide Specific Immunologic Memory, *Journal of Immunology* 138:4012–4017, (Jun., 1987).

Sprent, et al., Properties of Purified T Cell Subsets, I. In Vitro Responses to Class I vs. Class II H–2 Alloantigens, *J. Exp. Med.* 162:2068–2088, (Dec., 1985).Andrus, et al., Cytotoxic T Cells Both Produce And Respond To Interleukin 2, *J. Exp. Med.* 59:647–652, (Feb., 1984).

von Boehmer, et al., Lyt–2$^-$ T Cell–Independent Functions of Lyt–2$^+$ Cells Stimulated With Antigen Or Concanavalin A, *Journal of Immunology* 133:59–64.

Matis, et al., Adoptive Immunotherapy of a Syngeneic Murine Leukemia with a Tumor–Specific Cytotoxic T Cell Clone and Recombinant Human Interleukin 2: Correlation with Clonal IL2 Receptor Expression, *Journal of Immunology* 136:3496–3501, (May, 1986).

Mizuochi, et al., Role of Lymphokine–Secreting CD8+ T Cells in Cytotoxic T Lymphocyte Responses Against Vaccinia Virus, *Journal of Immunology* 142:270–273, (Jan., 1989).

Zinkernagel, et al., MHC–Restricted Cytotoxic T Cells: Studies on the Biological Role of Polymorphic Major Transplantation Antigens Determining T–Cell Restriction–Specificity, Function, and Responsiveness, *Advances in Immunology* 27:51–177, (1979).

Male, et al., Cytotoxic Lymphocytes, (*Advanced Immunology*, Chapter 7, Gower Publ., London; 1987).

Jacobson, et al., Measles Virus–Specific T4+ Human Cytotoxic T Cell Clones are Restricted by Class II HLA Antigens, *Journal of Immunology* 133:754–757, (Aug., 1984).

Gillis, et al., Long term culture of tumour–specific cytotoxic T cells, *Nature* 268:154–156, (Jul., 1977).

Cheever, et al., Augmentation of the Anti–Tumor Therapeutic Efficacy of Long–Term Cultred T Lymphocytes by In Vivo Administration of Purified Interleukin 2, *J. Exp. Med.* 155:968–980, (Apr. 1982).

Reddehase, et al., CD8–Positive T Lymphocytes Specific for Murine Cytomegalovirus Immediate–Early Antigens Mediate Protective Immunity, *Journal of Virology* 61:3102–3108, (Oct., 1987).

Rosenberg, et al., Use of Tumor–Infiltrating Lymphocytes and Interleukin–2 in the Immunotherapy of Patients with Metastatic Melanoma, *N. Engl. J. Med.* 319:1676–1680, (Dec., 1988).

Klarnet, et al., Helper–Independent CD8+ Cytotoxic T Lymphocytes Express IL–1 Receptors and Require IL–1 for Secretion of IL–2, *Journal of Immunology* 142:2187–2191, (Apr., 1989).

Alderson, et al., Interleukin 7 Enhances Cytolytic T Lymphocyte Generation and Induces Lymphokine–activated Killer Cells from Human Peripheral Blood, *J. Exp. Med.* 172:577–587, (Aug. 1990).

Walker, et al., HIV–specific cytotoxic T lymphocytes in seropositive individuals, *Nature* 328:345–348, (Jul., 1987).

Plata, et al., AIDS virus–specific cytotoxic T lymphocytes in lung disorders, *Nature* 328:348–351, (Jul., 1987).

Siliciano, et al., Analysis of Host–Virus Interactions in AIDS with Anti–gp120 T Cell Clones: Effect of HIV Sequence Variation and a Mechanism for CD4+ Cell Depletion, *Cell* 54:561–575, (Aug., 1988).

Walker, et al., Long–term culture and fine specificity of human cytotoxic T–lymphocyte clones reactive with human immunodeficiency virus type 1, *Proc. Natl. Acad. Sci. USA* 86:9514–9518, (Dec., 1989).

Chenciner, et al., Multiple subsets of HIV–specific cytotoxic T lymphocytes in humans and in mice, *Euro. J. Immunol.* 19:1537–1544, (1989).

Klarnet, et al., *Role of Interleukin–2 Activated Killer Cells in Cancer*, Lotzova and Herberman, eds. CRC Press; pp. 199–218, (1990).

Dower, et al., The interleukin–1 receptor, *Immunology Today* 8:46–51, (1987).

Bomsztyk, et al., Evidence for different interleukin 1 receptors in murine B– and T–cell lines, *Proc. Natl. Acad. Sci. USA* 86:8034–8038, (1989).

Lowenthal, et al., Expression of Interleukin 1 Receptors is Restricted to the L3T4+ Subset of Mature T Lymphocytes, *Journal of Immunology* 138:1–3, (1987).

Yamasaki, et al., Cloning and Expression of the Human Interleukin–6 (BSF–2/IFN$\beta$ 2) Receptor, *Science* 241:825–828, (1988).

Smith, et al., A Receptor for Tumor Necrosis Factor Defines an Unusual Family of Cellular and Viral Proteins, *Science* 248:1019–1023, (1990).

Loetscher, et al., Molecular Cloning and Expression of the Human 55 kd Tumor Necrosis Factor Receptor, *Cell* 61:351–359, (1990).

Schall, et al., Molecular Cloning and Expression of a Receptor for Human Tumor Necrosis Factor, *Cell* 61:361–370, (1990).

von Ruden, et al., Expression of functional human EGF receptor on murine bone marrow cells, *The EMBO Journal* 7:2749–2756, (1988).

Pierce, et al., Signal Transduction Through the EGF Receptor Transfected in IL–3–Dependent Hematopoietic Cells, *Science* 239:628–631, (1988).

Kurt–Jones, et al., Heterogeneity of Helper/Inducer T Lymphocytes, I. Lymphokine Production and Lymphokine Responsiveness, *Journal of Experimental Medicine* 166:1774–1787, (1987).

Greenbaum, et al., Autocrine Growth of CD4+ T Cells: Differential Effects of IL–1 on Helper and Inflammatory T Cells, *Journal of Immunology* 140:1555–1560, (1988).

Williams, et al., Introduction of new genetic material into pluripotent haematopoietic stem cells of the mouse, *Nature* 310:476–480, (1984).

Dick, et al., Introduction of a Selectable Gene into Primitive Stem Cells Capable of Long–Term Reconstitution of the Hematopoietic System of W/W$^v$ Mice, *Cell* 42:71–79, (1985).

Keller, et al., Expression of a foreign gene in myeloid and lymphoid cells derived from multipotent haematopoietic precursors, *Nature* 318:149–154, (1985).

Rosenberg, et al., Gene Transfer into Humans—Immunotherapy of Patients with Advanced Melanoma, Using Tumor–Infiltrating Lymphocytes Modified by Retroviral Gene Transduction, *New England Journal of Medicine* 323:570–578, (1990).

Miller, et al., Retrovirus Packaging Cells, *Human Gene Therapy* 1:5–14, (1990).

Kasid, et al., Human gene transfer: Characterization of human tumor–infiltrating lymphocytes as vehicles for retroviral–mediated gene transfer in man, *Proc. Natl. Acad. Sci. USA* 87:473–477, (1990).

Fearon, et al., Interleukin–2 Production by Tumor Cells Bypasses T Helper Function in the Generation of an Antitumor Response, *Cell* 60:397–403, (1990).

Russell, Lymphokine gene therapy for cancer, *Immunology Today* 11:196–200, (1990).

The L.IL-1RSN Retroviral Vector

METHOD FOR PRODUCING $T_H$-INDEPENDENT CYTOTOXIC T LYMPHOCYTES

ACKNOWLEDGEMENT OF GOVERNMENT SUPPORT

This invention was made in part with U.S. government support under grant number RO1 CA33084 awarded by the National Institutes of Health. The U.S. government has certain rights in the invention.

CROSS REFERENCE TO RELATED APPLICATION

This application is a continuation of application Ser. No. 08/055,903, filed Apr. 29, 1993, now abandoned, which is a continuation Ser. No. 07/764,596, filed Sep. 24, 1991, now abandoned, which is a continuation-in-part of application Ser. No. 07/614,167, filed Nov. 9, 1990, now abandoned, which is a continuation-in-part of application Ser. No. 07/589,939 filed Sep. 28, 1990, now abandoned.

BACKGROUND OF THE INVENTION

The mammalian hematopoietic system contains a variety of cell types which include myeloid and lymphoid cells. These cells act as effectors of immune responses and are responsible for combating infection and disease. The lymphoid cells are comprised of mature B and T lymphocytes, each cell bearing receptors specific for distinct antigens. The lymphocyte population plays an important role in mounting a humoral and cell-mediated response to foreign antigens.

All mature T lymphocytes express the CD3 cell surface molecule, but consist of two basic subtypes based on their mutually exclusive expression of cell surface molecules CD4 and CD8. $CD4^+$ T cells are generally involved in "helper" functions in immune responses and secrete cytokine molecules, in particular IL-2, IL-4 or IL-7, upon which the cytotoxic $CD8^+$ T cells are dependent. $CD4^+$ are often referred to as T helper ($T_H$) cells. $CD8^+$ cells are involved in "effector" functions in immune responses, such as direct cytotoxic destruction of target cells bearing foreign antigens, and represent an important mechanism for resistance to viral infections and tumors. The functional distinction between $CD4^+$ and $CD8^+$ T cells is based on the ability of $CD4^+$ cells to recognize antigen presented in association with class II MHC molecules, and $CD8^+$ cells to recognize antigen presented in association with class I MHC molecules. The $CD8^+$ cells that mediate this lyric function are designated cytotoxic T lymphocytes (CTLs). Although most CTL are of the $CD8^+$ phenotype, some CTL of the $CD4^+$ phenotype have been described. Generally, individual CFLs (whether $CD8^+$ or $CD4^+$) are antigen-specific.

CTLs are dependent on helper T ($T_H$) cell-derived cytokines, such as IL-2, IL-4 and IL-7, for growth and proliferation in response to foreign antigens. (Zinkernagel and Doherty, *Adv. Immunol.* 27:51, 1979; Male et al., *Advanced Immunology*, Chap. 7, Gower Publ., London, 1987; Jacobson et al., *J. Immunol.* 133:754, 1984). IL-2, for example, is a potent mitogen for cytotoxic T lymphocytes (Gillis and Smith, *Nature* 268:154, 1977), and the combination of antigen and IL-2 cause proliferation of primary $CD8^+$ T cells in vitro. The importance of IL-2 for the growth and maintenance of the $CD8^+$ CTL in vivo has been documented in models of adoptive immunotherapy in which the therapeutic efficacy of transferred anti-retroviral $CD8^+$ cells is enhanced on subsequent administration of IL-2 (Cheever et al., *J. Exp. Med.* 155:968, 1982; Reddehase et al., *J. Virol.* 61:3102, 1987). IL-4 and IL-7 are also capable of stimulating the proliferation of mature $CD8^+$ CTL (Alderson et al., *J. Exp. Med.* 172:577, 1990).

Due to the specificity of T cells for foreign antigens, considerable research has been focused on the use of T cells in treating viral infections and malignant tumors. Cytotoxic T cells specific for a particular type of tumor antigen can be isolated and administered to a patient having the tumor, with the effect that the CTLs ameliorate the tumor. It has been demonstrated, for example, that tumor-specific T cells can not only be generated to experimental tumors in mice, but also that T cells with apparent tumor specificity can be isolated from cancer patients. Such human tumor-infiltrating lymphocytes (TILs) have been expanded in vitro and used to treat cancer patients, generating significant enthusiasm for human adoptive immunotherapy with tumor-specific T cells (Rosenberg, et al., *N. Engl. J. Med.* 319:1767, 1988).

Similar studies using cytotoxic T cells specific for viral antigens have also been conducted in animal models. Human HIV specific CTL of both the $CD8^+$ (Walker et al., *Nature* 328:345, 1987; Plata et al., *Nature* 328:348, 1987) and $CD4^+$ (Siliciano et al., *Cell* 54:561, 1988) phenotype have been isolated and characterized. HIV-specific CTL are classical CTL in that their proliferative and cytotoxic responses are antigen-specific and MHC-restricted (Walker et al., supra; Plata et al., supra; Chenciner et al., *Eur. J. Immunol.* 19:1537, 1989; Walker et al., *Proc. Natl. Acad. Sci. USA* 86:9514, 1989), in common with the numerous mouse and human CTL clones which have been characterized which are specific for viral, tumor or allospecific antigens.

Although many antigen-specific T cell clones have been isolated, the use of tumorspecific T cell clones generated in vitro has been shown to have definite limitations in tumor therapy. It has been demonstrated in several therapeutic models that the efficacy of cytolytic $CD8^+$ T cells is limited by a dependency on exogenous IL-2 (produced by $T_H$ cells), a finding that has been substantiated in human adoptive therapy trials in which administration of exogenous IL-2 appears essential for optimal therapeutic efficacy (Rosenberg, et al., *N. Engl. J. Med.* 319:1767, 1988; Klarnet et al., in *Role of Interleukin-2 Activated Killer Cells in Cancer*, Lotzova and Herberman (eds.), CRC Pres, Florida, Chap. 14, pp. 199–218, 1990). Thus, while in vitro T cell cloning techniques provide a means to generate large numbers of T cells with demonstrable tumor or viral specificity, the full potential of using such antigen-specific T cells in therapy appears to be limited by their dependency on $T_H$ cells.

In some limited instances the problem of $T_H$ dependency may be circumvented by using a particular class of cells known to function independent of $T_H$ cells. These cells are known as helper-independent cytolytic $CD8^+$ T cells ($HIT_c$) (Klarnet et al., *J. Immunol.* 142:2187, 1989) and have been identified in populations of primary (i.e., freshly isolated from in vivo sources) $CD8^+$ CTL (Sprent and Schaefer, *J. Exp. Med.* 162:21068, 1985; Andros et al., *J. Exp. Med.* 159:647, 1984). $HIT_c$ cells produce sufficient IL-2 to grow independently of $CD4^+$ cells and the cytokines they produce. $HIT_c$ cells are also known to express plasma membrane IL-1 receptors (IL-1R) and require IL-1 for their IL-2-independent proliferation (Klarnet et al., 1989, supra). This is in contrast to conventional $CD8^+$ CTL which do not express detectable IL-1R on their surface (Lowenthal and MacDonald, 1987). $HIT_c$ cells have been generated which are specific for a range of antigens, including tumor, viral and alloantigens (von Boehmer et al., *J. Immunol.* 133:59, 1984; Klarnet et al., *J. Immunol.* 138:4012, 1987; and Andrus et al., *J. Exp. Med.* 159:647, 1984; Mizuochi et al., *J. Immunol* 142:270, 1989). $HIT_c$ specific for a retrovirally transformed tumor have been shown to eradicate the tumor cells and persist long-term in vivo following their engraftment (Klarnet et al., 1989, supra). Unfortunately, $HIT_c$ cells having specificity for many important antigens, such as HIV, have not yet been isolated.

In order to realize the full potential of antigen-specific T cells in therapy, it will be necessary to develop a more complete repertoire of $T_H$-independent cytolytic T cells.

SUMMARY OF THE INVENTION

The present invention provides a method for producing a T helper ($T_H$) cell-independent cytotoxic T lymphocyte (CTL) from a $T_H$-dependent CTL. The resulting $T_H$-independent CTLs are capable of enhanced growth or proliferation independent of $T_H$ cells.

Specifically, the present invention provides a method for producing a $T_H$-independent CTL by introducing into a $T_H$-dependent CTL a recombinant expression vector, for example, an infectious recombinant retroviral vector, encoding a cytokine receptor, such as an exogenous IL-1 receptor, which is capable of enhancing growth or proliferation of the CTL independent of $T_H$ cells. In preferred embodiments the CTL is antigen-specific and, upon expression of the cytokine receptor, the antigen-specific CTL is capable of enhanced growth or proliferation independent of $T_H$ cells.

The present invention also provides $T_H$-independent CTLs produced by the above method. The CTLs express a receptor, for example, IL-1 receptor, which is encoded by an exogenous expression vector introduced by gene transfer. The CTL, upon expression of the receptor, is capable of enhanced growth or proliferation independent of $T_H$ cells. In preferred embodiments the CTL is antigen-specific and, upon expression of the cytokine receptor, the antigen-specific CTL is capable of enhanced proliferation independent of $T_H$ cells.

The present invention also provides a method of selectively killing cells expressing a foreign antigen, for example, a tumor or viral antigen, in a mammal. CTLs having cytolytic specificity for cells expressing the antigen are isolated from a donor exposed to the antigen. A recombinant expression vector encoding an exogenous cytokine receptor capable of enhancing growth or proliferation of the CTLs, for example, IL-1R, is then introduced into the CTLs. The resulting $T_H$-independent CTLs are then introduced into a mammal in a sufficient number to kill cells expressing the antigen.

DETAILED DESCRIPTION OF THE INVENTION

Definitions

Figure 1:
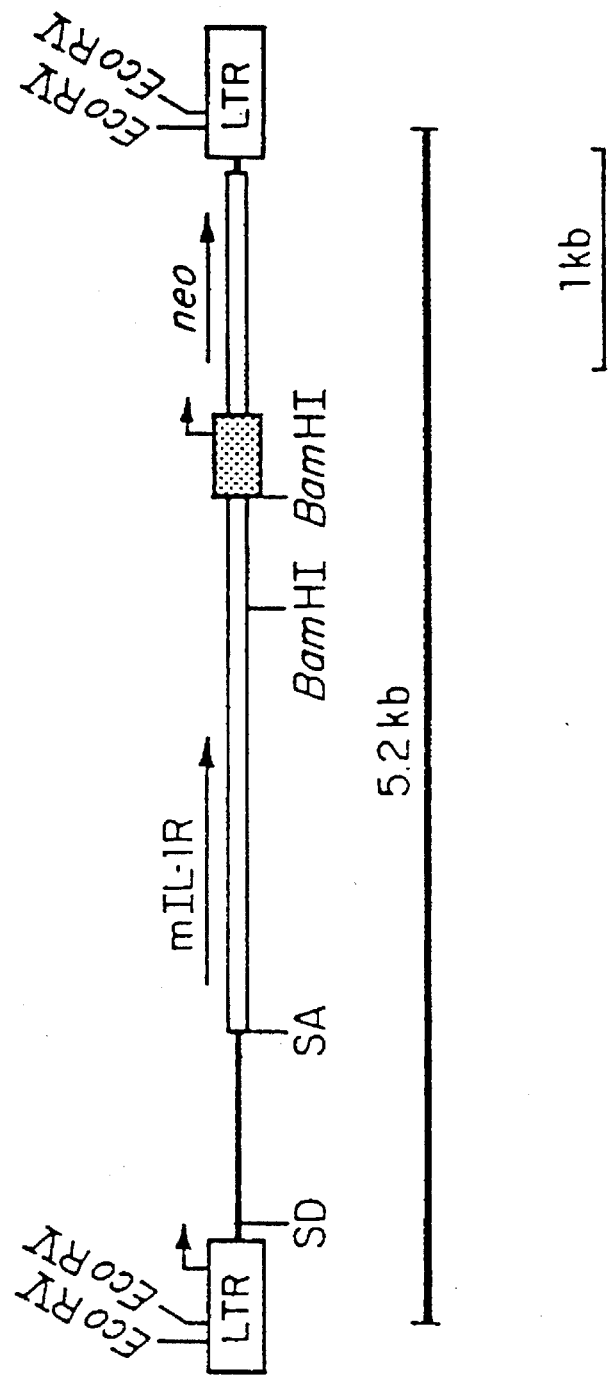
FIG. 1 is a schematic diagram of the plasmid form of the retroviral vector L.IL-1RSN which was introduced into the retroviral packaging cell lines PA317 and ψ2. Arrows indicate transcriptional start sites and direction of transcription. The open box labeled LTR is the retroviral long terminal repeat. SD is the splice donor, SA is the splice acceptor, and the stippled box is the SV40 early region promoter.

"Cytotoxic T lymphoctyes" or "CTLs" are T cells which bear the CD3 cell surface determinant and mediate the lysis of target cells bearing cognate antigens. CTLs may be of either the CD8$^+$ or CD4$^+$ phenotype. CTLs are generally antigen-specific and MHC-restricted in that they recognize antigenic peptides only in association with the Major Histocompatibility Complex (MHC) molecules on the surface of target cells. CTLs may be specific for a wide range of viral, tumor or allospecific antigens, including HIV, EBV, CMV and a wide range of tumor antigens. Some CTLs, however, may not be antigen specific, for example, some cloned CTLs can be induced to lose some of their specificity for their cognate antigen by culture in abnormally high concentrations of IL-2 (Brooks et al, Immunol. Rev. 72:43, 1983).

The term "recombinant expression vector" refers to a replicable unit of DNA or RNA in a form which is capable of being introduced into a target cell by transfection, transduction or retroviral infection, and which codes for the expression of a heterologous structural coding sequence, for example, a cytokine receptor, which is transcribed into mRNA and translated into protein under the control of a genetic element or elements having a regulatory role in gene expression, such as promoters or enhancers. Such vectors will preferably also contain appropriate transcription and translation initiation and termination sequences. The recombinant expression vectors of the present invention can take the form of DNA constructs replicated in bacterial cells and transfected into target cells directly, for example, by calcium phosphate precipitation, electroporation or other physical transfer methods, or RNA constructs in the form of infectious retroviruses packaged by suitable "packaging" cell lines producing the retroviral vector. Vectors used for direct transfection will include DNA sequences enabling replication of the vector in the bacterial host cells. Various recombinant expression vectors suitable for use in the present invention are described below.

"Recombinant," as used herein, means that a particular DNA sequence is the product of various combinations of cloning, restriction, and ligation steps resulting in a construct having a structural coding sequence distinguishable from homologous sequences found in natural systems. Generally, DNA sequences encoding the structural coding sequence, for example cytokine receptor proteins, can be assembled from cDNA fragments and short oligonucleotide linkers, or from a series of oligonucleotides, to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where such sequences do not interfere with manipulation or expression of the coding regions.

A "$T_H$ independent" CTL is capable of enhanced growth or proliferation in the presence of limiting quantities or the absence of CD4$^+$ T helper ($T_H$) cell-derived cytokines or their equivalents or is capable of enhanced growth or proliferation relative to parental CTLs from which the subject CTL was derived. Growth or proliferation may be measured, for example, by any in vitro proliferation or growth assay or by any assay measuring the the ability of the CTL to persist in vivo. Specific examples of suitable assays are disclosed below in Examples 3 and 4. CTLs capable of enhanced growth or viability may have augmented ability to destroy target cells bearing foreign antigens or provide long term immunologic memory.

A "cytokine receptor" means a cell surface protein which is capable of binding a cytokine molecule and assisting in transducing the signal provided by the cytokine molecule.

Cytokine receptors which are capable of enhancing growth or proliferation of CTLs in a $T_H$-independent manner, as defined above, include, for example, type I and type II Interleukin-1 Receptors. Other equivalent receptors include Interleukin-6 Receptor (IL-6R), and Tumor Necrosis Factor Receptors (TNF-R). The cytokine receptors of the present invention are preferably exogenous to the CTL.

A CTL is "cytolytically specific for" cells expressing tumor or viral antigens if the CTL is capable of selectively recognizing and lysing the cells bearing the tumor or viral antigen. A CTL is "cytolytically reactive against" cells expressing tumor or viral antigens if the CTL is capable of lysing the cells bearing the tumor or viral antigen, without regard to its ability to selectively recognize such cells.

Gene Transfer Methods

Numerous methods have been developed for introducing exogenous genes into mammalian cells, such as by transfection or by infection. These transduction methods may be physical in nature, or they may rely on the use of recombinant retroviral vectors encoding DNA which can be transcribed to RNA, packaged into infectious viral particles and used to infect target cells and thereby deliver the desired genetic material. Many different types of mammalian gene transfer and expression vectors have been developed (see, Miller and Calos, eds., "Gene Transfer Vectors for Mammalian Cells," *Current Comm. Mol. Biol.*, (Cold Spring Harbor Laboratory, New York, 1987)). Naked DNA can be physically introduced into mammalian cells by transfection using any one of a number of techniques including, but not limited to, calcium phosphate transfection (Berman et al., *Proc. Natl. Acad. Sci. USA* 84 81: 7176, 1984) DEAE-Dextran transfection, protoplast fusion (Deans et al., *Proc. Natl. Acad. Sci. USA* 84 81: 1292, 1984), electroporation (Potter et al., *Proc. Natl. Acad. Sci. USA* 84 81:7161, 1984), lipofection (Felgner et al., *Proc. Natl. Acad. Sci. USA* 84:7413, 1987), polybrene transfection (Kawai and Nishzawa, *Mol. Cell. Biol* 4:1172, 1984) and direct gene transfer by laser micropuncture of cell membranes (Tao et al., *Proc. Natl. Acad. Sci. USA* 84 84:4180, 1987). Various infection techniques have been developed which utilize recombinant infectious virus particles for gene delivery. This represents a preferred approach to the present invention. The viral vectors which have been used in this way include virus vectors derived from simian virus 40 (SV40; Karlsson et al., *Proc. Natl. Acad. Sci. USA* 84 82:158, 1985), adenoviruses (Karlsson et al., *EMBO J.* 5:2377, 1986), adeno-associated virus (LaFace et al., *Virology* 162:483, 1988) and retroviruses (Coffin, 1985, p17-71 in Weiss et al (eds.), *RNA Tumor Viruses*, 2nd ed., Vol 2, Cold Spring Harbor Laboratory, New York). Thus, gene transfer and expression methods are numerous but essentially function to introduce and express genetic material in mammalian cells. Several of the above techniques have been used to transduce hematopoietic or lymphoid cells, including calcium phosphate transfection (Berman et al., supra, 1984), protoplast fusion (Deans et al., supra, 1984), electroporation (Cann et al., *Oncogene* 3:123, 1988), and infection with recombinant adenovirus (Karlsson et al., supra; Ruether et al., *Mol. Cell. Biol.* 6:123, 1986) adeno-associated virus (LaFace et al., supra) and retrovirus vectors (Overell et al., *Oncogene* 4:1425, 1989). Primary T lymphocytes have been successfully transduced by electroporation (Cann et al., supra, 1988) and by retroviral infection (Nishihara et al., *Cancer Res.* 48:4730, 1988; Kasid et al., supra, 1990).

Retroviral Vectors

Retroviral vectors provide a highly efficient method for gene transfer into eukaryotic cells and is the preferred method for the delivery of a gene into primary cells. Moreover, retroviral integration takes place in a controlled fashion and results in the stable integration of one or a few copies of the new genetic information per cell.

Retroviruses are a class of viruses which replicate using a virus-encoded, RNA-directed DNA polymerase, or reverse transcriptase, to replicate a viral RNA genome to provide a double-stranded DNA intermediate which is incorporated into chromosomal DNA of an avian or mammalian host cell. Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of several species, including humans. A characteristic feature of retroviral genomes (and retroviral vectors used as described herein) is the retroviral long terminal repeat, or LTR, which is an untranslated region of about 600 base pairs found in slightly variant forms at the 5' and 3' ends of the retroviral genome. When incorporated into DNA as a provirus, the retroviral LTR includes a short direct repeat sequence at each end and signals for initiation of transcription by RNA polymerase II and 3' cleavage and polyadenylation of RNA transcripts. The LTR contains all other cis-acting sequences necessary for viral replication.

A "provirus" refers to the DNA reverse transcript of a retrovirus which is stably integrated into chromosomal DNA in a suitable host cell, or a cloned copy thereof, or a cloned copy of unintegrated intermediate forms of retroviral DNA. Forward transcription of the provirus and assembly into infectious virus occurs in the presence of an appropriate helper virus or in a cell line containing appropriate sequences enabling encapsidation without coincident production of a contaminating helper virus. Mann et al. (Cell 33:153, 1983) describe the development of cell lines (e.g., ψ2) which can be used to produce helper-free stocks of recombinant retrovirus. These cell lines contain integrated retroviral genomes which lack sequences required in cis for encapsidation, but which provide all necessary gene products in trans to produce intact virions. The RNA transcribed from the integrated mutant provirus cannot itself be packaged, but these cells can encapsidate RNA transcribed from a recombinant retrovirus introduced into the same cell. The resulting virus particles are infectious, but replication-defective, rendering them useful vectors which are unable to produce infectious virus following introduction into a cell lacking the complementary genetic information enabling encapsidation. Encapsidation in a cell line harboring trans-acting elements encoding an ecotropic viral envelope (e.g., ψ2) provides ecotropic (limited host range) progeny virus. Alternatively, assembly in a cell line containing amphotropic packaging genes (e.g., PA317, ATCC CRL 9078; Miller and Buttimore, *Mol. Cell. Biol.* 6:2895, 1986) provides amphotropic (broad host range) progeny virus. Such packing cell lines provide the necessary retroviral gag, pol and env proteins in trans. This strategy results in the production of retroviral particles which are highly infectious for mammalian cells, while being incapable of further replication after they have integrated into the genome of the target cell. The product of the env gene is responsible for the binding of the retrovirus to viral receptors on the surface of the target cell and therefore determines the host range of the retrovirus. The PA317 cells produce retroviral particles with an amphotropic envelope protein, which can transduce cells of human and other species origin. Other packaging cell lines produce particles with ecotropic envelope proteins, which are able to transduce only mouse and rat cells.

Numerous retroviral vector constructs have been used successfully to express many foreign genes (see, e.g., Coffin, in Weiss et al. (eds.), *RNA Tumor Viruses*, 2nd Ed., Vol. 2, (Cold Spring Harbor Laboratory, New York, 1985, pp. 17–71). Retroviral vectors with inserted sequences are generally functional, and few sequences that are consistently inhibitory for retroviral infection have been identified. Functional polyadenylation motifs inhibit retroviral replication by blocking retroviral RNA synthesis, and there is an upper size limit of approximately 11 kb of sequence which can be packaged into retroviral particles (Coffin, supra, 1985); however, the presence of multiple internal promoters, initially thought to be problematic (Coffin, supra, 1985), was found to be well tolerated in several retroviral constructs (Overell et al., *Mol. Cell Biol.* 8:1803, 1983).

Retroviral vectors have been used as genetic tags by several groups to follow the development of murine hematopoietic stem cells which have been transduced in vitro with retrovirus vectors and transplanted into recipient mice (Williams et al., *Nature* 310:476, 1984; Dick et al., *Cell* 42:71, 1985; Keller et al., *Nature* 318:149, 1985). These studies have demonstrated that the infected hematopoietic cells reconstitute the hematopoietic and lymphoid tissues of the recipient animals and that the cells display a normal developmental potential in vivo. The marked cells can be visualized using any of a number of molecular biological techniques which can demonstrate the presence of the retroviral vector sequences, most notably Southern analysis and PCR (polymerase chain reaction). The ability to mark cells genetically using retroviral vectors is also useful in clinical settings in which the technique can be used to track grafts of autologous cells. This approach has already been used to track TILs (tumor infiltrating lymphocytes) in patients given TIL therapy for terminal cancer treatment by Rosenberg et al. (*N. Engl. J. Med.* 323:570, 1990. The transduction of these cells with the marker gene was not associated with in vitro cellular dysfunction (Kasid et al., *Proc. Natl. Acad. Sci. USA* 87:473, 1990).

Many gene products have been expressed in retroviral vectors. This can either be achieved by placing the sequences to be expressed under the transcriptional control of the promoter incorporated in the retroviral LTR, or by placing them under the control of a heterologous promoter inserted between the LTRs. The latter strategy provides a way of coexpressing a dominant selectable marker gene in the vector, thus allowing selection of cells which are expressing specific vector sequences. The retroviral vectors of the present invention preferably contain a dominant selectable marker for infected cells, for example, an antibiotic resistance phenotype such as neo and aph (which confers G418 resistance) (Southern and Berg, *J. Mol. Appl. Genet.* 1:327, 1982), hph (hygromycin resistance) (Sugden et al., *Mol. Cell. Biol.* 5:410, 1985) or gpt (mycophenolic acid resistance). Alternatively, the vector may contain a gene product which complements a metabolic deficiency in a specialized host strain, for example, thymidine kinase activity in tk$^-$ cells, or hypxanthine phosphoribosyl transferase (HPRT) activity in HPRT$^-$ cells. Such selectable markers are widely available.

Suitable retroviruses which can be adapted for use in the present invention may be derived from many arian or mammalian hosts. However, a requirement for use is that the virus be capable of infecting cells which are to be the recipients of the new genetic material to be transduced using the retroviral vector. Examples of retroviruses which may be used to derive suitable vectors for use in the present invention include arian retroviruses, such as arian erythroblastosis virus (AEV), avian leukosis virus (ALV), avian myeloblastosis virus (AMV), avian sarcoma virus (ASV), Fujinami sarcoma virus (FuSV), spleen necrosis virus (SNV), and Rous sarcoma virus (RSV); bovine leukemia virus (BLV); feline retroviruses, such as feline leukemia virus (FeLV) or feline sarcoma virus (FeSV); murine retroviruses, such as murine leukemia virus (MuLV); mouse mammary tumor virus (MMTV), and murine sarcoma virus (MSV); and primate retroviruses, such as human T-cell lymphotropic viruses 1 and 2 (HTLV-1, and -2), and simian sarcoma virus (SSV). Many other suitable retroviruses are known to those skilled in the art. A taxonomy of retroviruses is provided by Teich, in Weiss et al. (eds.), *RNA Tumor Viruses*, 2d ed., Vol. 2 (Cold Spring Harbor Laboratory, New York, 1985, pp. 1–160). Preferred retroviruses for use in connection with the present invention are the murine retroviruses known as Moloney murine leukemia virus (MoMLV), Moloney murine sarcoma virus (MoMSV), Harvey murine sarcoma virus (HaMSV) and Kirsten murine sarcoma virus (KiSV).

A particularly preferred retrovirus is the retroviral vector pLXSN, described by Miller and Rosman, *Biotechniques* 7:980, 1989. This retroviral vector is capable of expressing heterologous DNA under the transcriptional control of the retroviral LTR and the neo gene under the control of the SV40 early region promoter. Construction of useful replication defective retroviral vectors is a matter of routine skill. The resulting recombinant retroviruses are capable of integration into the chromosomal DNA of an infected host cell, but once integrated, are incapable of replication to provide infectious virus, unless the cell in which it is introduced contains another proviral insert encoding functionally active trans-acting viral proteins.

Gene Expression

The retroviral vectors used in accordance with the present invention will contain transcriptional control sequences having appropriate initiation signals, enhancers, and promoters, which induce or control transcription of downstream structural sequences with which they are operably linked. Such enhancers and or promoters can be derived from viral or cellular, including mammalian genomes, and are preferably constitutive in nature. Many different promoters have been used to express genes in retroviral vectors. In comparing a panel of vectors expressing the human factor IX cDNA, Palmer et al. (*Blood* 73:438, 1989) found similar levels of expression of factor IX in infected fibroblasts whether the cDNA was expressed under the control of the retroviral LTR or an internal human cytomegalovirus immediate-early (HCMV-IE) promoter; an internal SV40 early region promoter gave several fold lower expression levels. In similar studies, Hock et al. (*Blood* 74:876, 1989) expressed the ADA gene under the control of a variety of enhancers and promoters, which included the lymphotropic papovavirus enhancer and beta-globin promoter, in infected hematopoietic cell lines and observed up to a 20-fold difference in ADA expression in infected cells.

To be expressed in the transduced cell; DNA sequences introduced by any of the above gene transfer methods are usually expressed under the control of an RNA polymerase II promoter. Transcriptional control sequences which may be used in retroviral vectors include the histone H4 promoter (Guild et al., *J. Virol.* 62:3795, 1988), the mouse metallothionein promoter (Mc Ivor et al., *Mol. Cell. Biol.* 7:838, 1987), the rat growth hormone promoter (Miller et al., *Mol. Cell. Biol.* 5:431, 1985), the human adenosine deaminase promoter (Hantzapoulos et al., *Proc. Natl. Acad. Sci. USA* 86:3519, 1989) the HSV tk promoter (Tabin et al., *Mol. Cell. Biol.* 2:426, 1982), the alpha-1 antitrypsin enhancer (Peng et al., *Proc. Natl. Acad. Sci. USA* 85:8146, 1988) and the immunoglobulin enhancer/promoter (Blankenstein et al., *Nucleic Acid Res.* 16:10939, 1988), the SV40 early or late promoters, the Adenovirus 2 major late promoter, or other viral promoters derived from polyoma virus, bovine papilloma virus, or other retroviruses or adenoviruses. The entire Adenovirus 2 genome is available from BRL (#52705A). Similarly, there are numerous sources of SV40 DNA, including commercial vendors such as New England Biolabs. Using well-known restriction and ligation techniques, appropriate transcriptional control sequences can be excised from various DNA sources and integrated in operative relationship with the intact structural genes to be expressed using the retroviral constructs of the present invention. Thus, many transcriptional control sequences may be used successfully in retroviral vectors to direct the expression of inserted genes in infected cells.

Lymphokine Receptors

There are two forms of interleukin-1, $\alpha$ and $\beta$, which in biologically active form are of similar size of 17.5 kD. Two types of IL-1 receptors have been identified, type I and type II. The type I IL-1R has been extensively characterized (Dower et al., *Nature* 324:266, 1986; Dower et al., *J. Exp. Med.* 162:501, 1985) and cDNAs encoding the type I IL-1R have been molecularly cloned (Sims et al., *Science* 241:585, 1985; Sims et al., *Proc. Natl. Acad. Sci. USA* 86:8946, 1989). The type II IL-1R has recently been identified and characterized (Benjamin et al., *J. Biol. Chem.* 265:9943, 1990; Bomsztyk et al., *Proc. Natl. Acad. Sci. USA* 86:8034, 1989) and cDNAs encoding the type II IL-1R have been molecularly cloned (McMahon et al., *EMBO J.* 10:2821–2832, 1991; PCT/US91/03498, 1991). Either the type I or type II IL-1R may be used in connection with the present invention, although the type I IL-1R is preferred.

The receptor found on T cells (type I) is specific for IL-1 and does not bind any of a large panel of other growth factors which have been tested for their ability to compete with radiolabeled IL-1 for binding to its receptor. The IL-1R is widely displayed, being present on many cell types, generally in low numbers/cell (less than a few thousand as determined by Scatchard analysis; Dower et al., supra, 1985), but is not present on CTLs. Binding of IL-1 to its receptor does not generally directly trigger a cellular proliferative response, but rather induces the production of other cytokines by the target cell as has been shown for the transfected receptor (see below; Curtis et al., *Proc. Natl. Acad. Sci. USA* 86:3045, 1989).

The characterization of the type I IL-1R found on T cells culminated in the cloning of cDNAs encoding the receptor from the mouse EL4 T cell line (Sims et al., *Science* 241:585, 1988). The subsequent cloning of cDNAs encoding the IL-1R from human T cells (Sims et al., *Proc. Natl. Acad. Sci. USA* 86:8946, 1989) showed that it was structurally similar to the murine protein. The human IL-1 receptor is encoded by a single mRNA species and has a classical hydrophobic leader sequence, an extracellular portion consisting of 3 19 amino acids, a single internal hydrophobic membrane-spanning domain and an intracellular domain of 213 amino acids. The leader sequence is removed to give a mature cell surface receptor with an apparent $M_r$ of ~80 kD, of which approximately 15 kD consists of added carbohydrate moieties. Extracellularly, the receptor consists of three immunoglobulin-like domains and is a member of the Immunoglobulin superfamily. The cytoplasmic sequence is not significantly homologous to any other proteins in the databases, with no homology to the motifs found in tyrosine kinases, for example. The cloned receptor has been shown to be biologically capable of transmitting an IL-1 signal in transfected Chinese hamster fibroblasts, leading to IL-1 dependent stimulation of prostaglandin $E_2$ and G-CSF by the transfected cells (Curtis et al., *Proc. Natl. Acad. Sci. USA* 86:3045, 1989).

Interleukin-6 shares many biological properties with IL-1 and TNF (Dinarello, *Adv. Immunol.* 44:153, 1989). IL-6 and its corresponding receptors also regulate the growth and differentiation of various tissues, including T cells, and may function in an equivalent manner as IL-1 receptors in converting $T_H$ dependent CTLs to $T_H$ independence. Like IL-1, IL-6 has been shown to induce IL-2 production in mitogen-stimulated T cells and thymocytes (German et al., *Proc. Natl. Acad. Sci. (USA)* 84:7629, 1987). A complementary DNA encoding the human IL-6 receptor has been isolated (Yamasaki et al., *Science* 241:825, 1988).

Tumor Necrosis Factor (TNF) and its corresponding receptors also have a wide range of biological activities in inflammation and immunologic responses, and functions primarily by stimulating the production of other cytokines. The biological activities of TNF are mediated by two distinct cell surface receptors having molecular weights of 55 kDa and 75 kDa, referred to as p55 and p75, respectively. Both the p55 and p75 forms of TNF receptor have been molecularly cloned and expressed (Smith et al., *Science* (Wash. D.C.) 248:1019, 1990; Loetscher et al., *Cell* 61:351, 1990; Schall et al., *Cell* 61:361, 1990).

Adoptive Immunotherapy

Adoptive immunotherapy is a therapeutic regimen involving the isolation, and in vitro cloning and expansion of immunologically active cells from a patient. The expanded, therapeutically active cells are reintroduced into the patient to obtain a therapeutic effect. In accordance with the present invention, CTLs are transduced with a recombinant expression vector encoding a cytokine receptor, for example, IL-1R, enabling growth of the transfected CTL independent of $T_H$ cells. Such CTLs are expected to be useful in adoptive immunotherapy where growth or in vivo function of the CTL are needed for mounting an immune response, and, in particular, where $T_H$ dependent growth or in vivo function are compromised by complete or partial failure of $T_H$ help, for example, as a result of HIV infection. By converting the $T_H$ dependent CTL to $T_H$ independence, the CTL can function independent of $T_H$ help. The CTLs may be antigen non-specific, but are preferably antigen-specific. In a particularly preferred embodiment of the present invention, a human being is treated for a disease characterized in part by the presence of a foreign antigen. In accordance with this method, CTLs having specificity for a distinct antigen are isolated from a subject. Suitable antigen-specific CTLs may have specificity for viral or tumor antigens. A recombinant expression vector encoding IL-1 receptor is introduced into the CTL, thereby converting the CTL to a $T_H$-independent phenotype, and enabling growth or in vivo function of the CTL independent of T cell help. The resulting $T_H$ independent antigen-specific CTLs are then introduced into a human being having a disease characterized by the presence of the antigen for which the CTL have specificity.

The majority of viral infections encountered by humans are rapidly controlled by the host immune response. In particular, the development of MHC-restricted virusspecific $CD8^+$ CTL and $CD4^+$ helper ($T_H$) T cell responses correlate with the resolution of acute viral infections (Ada and Jones, *Curr. Top. Microbiol. Immunol.* 128:1, 1986; Howes et al. *Nature* 277:67, 1979). For human viruses such as CMV or EBV with latent or persistent phases like HIV, a class I MHC restricted $CD8^+$ $T_C$ memory response is necessary to maintain latency and limit viral spread following reactivation (Howes et al., *Nature* 277:67, 1979; Rook et al., *Transplantation Proceedings* 16:1466, 1984). Similarly, in individuals infected with HIV, $CD8^+$ T lymphocytes contribute to the control of HIV replication by direct lysis of infected cells and by suppressing viral replication (Walker et al., *Nature* 328:345, 1987; Walker et al., *Science* 234:1563, 1986). Although $CD8^+$ MHC restricted HIV-specific $T_C$ responses are elicited in healthy HIV seropositive individuals as demonstrated by analysis of peripheral blood lymphocytes, these responses are decreased or absent in AIDS patients (Paltaleo et al., *J. Immunol.* 144:1696, 1990). This decline in $CD8^+$ HIV-specific $T_C$ reactivity may result from the tropism of HIV for $CD4^+$ $T_H$ cells, since functional in vivo $CD8^+$ $T_C$ responses are dependent on the presence of adequate helper function through cytokine release (e.g., IL2 and IL-4) provided by $CD4^+$ $T_H$. Thus, the gradual loss of $CD4^+$ $T_H$ function as a consequence of HIV infection may lead to the inability of the host to generate and maintain sufficient HIV-specific $CD8^+T_C$ to control infection.

Experiments carried out in murine models of viral infection have demonstrated that adoptively transferred syngeneic immune T cells can prevent and treat viral diseases and illustrate the potential for utilizing T cell therapy in human viral infections. Antiviral effects of adoptive immunotherapy have been demonstrated in murine models of infections with influenza, lymphocytic choriomeningitis virus (LCMV), respiratory synctytial virus (RSV), and murine cytomegalovirus (MCMV) (Lukacher et al., *J. Exp. Med.* 160:814, 1984; Larsen et al., *J. Virology* 50:56, 1984; Byrne and Oldstone, *J. Virology* 51:682, 1984; Cannon et al., *Immunology* 62:133, 1987; Reddehase et al., *J. Virol.* 55:264, 1985). Studies to determine the contribution to therapeutic efficacy of the $CD8^+$ $T_C$ or $CD4^+$ $T_H$ subsets have been most rigorously evaluated in the MCMV model. These studies have shown that the protective and therapeutic antiviral effects of adoptive T cell transfer can be mediated by the MCMV-specific $CD8^+$ $T_C$ subset alone (Reddehase et al., *J. Virol.* 55:264, 1985; Reddehase et al., *J. Virol.* 61:3102, 1987). The adoptive transfer of MCMV-immune $CD4^+$ $T_H$ cells alone did not have measurable direct antiviral effects at the cell doses evaluated. However, $CD4^+$ $T_H$ T cells produce lymphokines including IL-2, IL-4, IL-5, GM-CSF and gamma interferon, and could contribute to therapeutic efficacy through the antiviral effects of gamma interferon, or the growth-promoting effects of IL-2 and IL-4 on virus-specific $CD8^+$ $T_C$ (Smith, *Immunol. Rev.* 51:337, 1980; Widmer and Grabstein, *Nature* 326:795, 1987). Thus, the cotransfer of lymphokine-producing $CD4^+T_H$ can augment the efficacy of $CD8^+$ $T_C$ by promoting in vivo proliferation and viability of transferred $CD8^+$ cells. Alternatively, as has been demonstrated in the MCMV model, the efficacy of the $CD8^+$ $T_C$ subset can be improved by the concurrent systemic administration of IL-2, with achievement of equivalent antiviral effects after transfer of lower doses of $CD8^+$ cells (Reddehase et al., *J. Exp. Med.* 165:650, 1987). Similar studies have explored the use of virus-specific $CD8^+$ $T_C$ clones to treat influenza virus and respiratory synctytial virus pneumonia. Studies in mice with established influenza virus pneumonia given $CD8^+$ influenza-specific $T_C$ clones have demonstrated no adverse effects and a rapid improvement in pulmonary histologic abnormalities, evident as early as six days following cell transfer with complete normalization of lung pathology by day 10 (MacKenzie et al., *Immunology* 67:375, 1989). Similarly, treatment of mice with RSV pneumonitis with low doses of $CD8^+$ RSV-specific $T_C$ resulted in reduced viral titres in the lung and resolution of infection without worsening pulmonary function (Cannon et al., *J. Exp. Med.* 168:1163, 1988).

To analyze the persistence of transferred T cells specific for FBL, a murine retrovirally-induced tumor, a model in which donor T cells were congenic for the Thy-1 antigen of the host was used and revealed that donor tumor-reactive T cells persisted long after the time required for tumor eradication and could serve as memory T cells in the host (Greenberg et al., *Cancer Res.* 40:4428, 1980). Examination of the mechanisms by which immune T cells eliminate tumor has revealed that noncytotoxic $CD4^+$ $T_H$ cells can mediate a curative antitumor effect in adoptive immunotherapy by inducing an inflammatory delayed type hypersensitivity response, whereas purified immune $CD8^+$ $T_C$ depleted of $T_H$ produce a demonstrable but more limited antitumor effect (Greenberg et al., *J. Exp. Med.* 154:952, 1981; Greenberg et al., *J. Exp. Med.* 161:1122, 1985; Greenberg, *J. Immunol.* 136:1917, 1986). However, the efficacy of $T_C$ can be markedly augmented by either the concurrent transfer of $T_H$ or the in vivo administration of recombinant IL-2, which are necessary to support the in vivo survival and proliferation of $T_C$ (Greenberg, *J. Immunol.* 136:1917, 1986).

Recent studies have examined the efficacy of helper-independent $CD8^+$ $T_C$ clones ($HIT_c$) in therapy. These $CD8^+$ $T_C$ clones produce IL-2 following antigen activation, can be generated by repetitive cycles of stimulation with antigen, and can rest long-term in the absence of IL-2 or antigen stimulation (Matis et al., *J. Immunol.* 136:3490, 1986; Klarnet et al., *J. Immunol.* 138:4012, 1987). Adoptive transfer of $HIT_C$ alone results in eradication of disseminated FBL and provides the host with long-term in vivo immunologic memory (Klarnet et al., *J. Immunol.* 138:4012, 1987). Thus, studies in this murine retrovirus tumor model have demonstrated the feasibility of using in vitro expanded, antigen-specific T cells for adoptive therapy to mediate a therapeutic effect and provide persistent immunity. Moreover, the studies with IL-2 producing $CD8^+$ $T_C$ ($HIT_c$) clones illustrate the potential for providing effective therapy and long-lasting immunity with $CD8^+$ class I MHC restricted cytolytic effector cells alone.

Treatments for AIDS are currently only palliative in nature, mostly involving the use of nucleoside analogs such as AZT to interfere with HIV replication. Adoptive immunotherapy offers the potential of providing a new virus-specific modality to the treatment of AIDS. One approach to adoptive immunotherapy is to augment host HIV-specific CTL activity by expanding autologous antigen-specific $CD8^+$ CTL in vitro and then returning them to the host. It is well established that $CD8^+$, HIV-specific CTL can be detected in healthy HIV-seropositive patients, and that these cells can be directed to kill HIV-antigen expressing target cells in vitro (Chenciner et al., 1989). In addition, HIV-specific CTL have been shown to inhibit replication of HIV in human lymphocytes in culture (Tsubota et al., *J. Exp. Med.* 169:1421, 1989) and there is circumstantial evidence that CTL may retard the development of AIDS in vivo (Hoffenbach et al., *J. Immunol.* 142:452, 1989). In combination with the data from mouse models cited above, these findings argue that $CD8^+$ CTL function in HIV-infected individuals should have an antiviral effect.

Effective adoptive immunotherapy of HIV infection will require the identification and subsequent in vitro expansion of a potentially small number of HIV-specific effector T cells present in the host to numbers sufficient to mediate a therapeutic effect. Studies in the murine FBL model have examined the efficacy of cultured T cells and T cell clones in adoptive immunotherapy. Techniques have been developed to expand immune T cells to large numbers by specific activation in vitro with antigen, followed by repetitive cycles of restimulation with antigen, mononuclear feeder cells and IL-2 (Cheever et al., *J. Immunol.* 126:1318, 1981; Cheever et al., *J. Exp. Med.* 155:968, 1982; Cheever et al., *J. Exp. Med.* 163:1100, 1986). T cells cultured long-term under the above conditions retained specificity in vitro following expansion, and mediated a specific dose-dependent effect in adoptive immunotherapy of disseminated tumor (Cheever et al., *J. Immunol.* 126:1318, 1981; Cheever et al., *J. Exp. Med.* 155:968, 1982; Cheever et al., *J. Exp. Med.* 163:1100, 1986). Moreover, IL-2, which promotes rapid in vitro proliferation, augmented the therapeutic efficacy of cultured T cells if administered to the host following cell transfer (Cheever et al., *J. Exp. Med.* 155:968, 1982). This combined approach of T cells plus IL-2 has made it possible to cure disseminated leukemia by infusion of a relatively small number of donor T cells, thereby obviating the need to generate large numbers of effector cells in vitro. Moreover, long-term cultured T cells administered to tumor-beating mice distributed widely in host lymphoid organs, persisted for greater than 100 days after discontinuation of IL-2 administration, and provided the host with antigenspecific immunologic memory (Cheever et al., *J. Exp. Med.* 155:968, 1982).

Cellular immunotherapy has not yet been evaluated for patients with viral infections, but immune effector T cells are being used to treat patients with advanced malignancies. A major goal of tumor therapy is to transfer tumor-specific MHC restricted T cells similar to the MHC restricted HIV-specific T cells, but the clinical trials thus far have frequently used non-MHC restricted populations of cytolytic effector cells, in part due to the difficulties identifying human tumor antigens that will effectively induce MHC restricted T cell responses. Despite these differences, the studies in cancer patients provide some insights into the safety and toxicity of infusing large numbers of activated cytolytic effector cells (Mazumder et al., *Cancer* 53:896, 1984; Rosenberg et al., *N. Engl. J. Med.* 313:1485, 1985).

Studies of cellular immunotherapy in cancer patients have evaluated two effector populations. Lymphokine activated killer (LAK) cells, generated by short-term culture of PBMC in the presence of high concentrations of IL-2, lyse transformed target cells and have minimal lytic activity for most normal tissues (Grimm et al., *J. Exp. Med.* 155:1823, 1982; Sondel et al., *J. Immunol.* 137:502, 1986). The adoptive transfer of in vitro generated LAK cells has demonstrated the safety of systemically administering large numbers of in vitro activated lymphocytes. Up to $10^{11}$ LAK cells have been administered in a single intravenous infusion to cancer patients with minor systemic toxicity and no pulmonary compromise due to trapping in the pulmonary vasculature (Mazumder et al., *Cancer* 53:896, 1984; Rosenberg et al., *N. Engl. J. Med.* 313:1485, 1985). Therapeutic trials have also combined short courses of high dose systemic IL2 administration with LAK cell transfer to promote LAK function and viability with apparent enhanced efficacy (Rosenberg et al., *N. Engl. J. Med.* 313:1485, 1985; Rosenberg et al., *N. Engl. J. Med.* 316:1310, 1986).

Therapy with in vitro expanded lymphocytes derived from a tumor infiltrate has also been explored. The rationale for using such tumor infiltrating lymphocytes (TIL) is that these lymphocytes might be enriched for tumor-reactive T cells, and such TIL cells have been shown in a murine sarcoma model to be 50–100 times more effective than LAK cells in eradicating tumor micrometastases (Sondel et al., *J. Immunol.* 137:502, 1986). In humans, TIL cell lines have been generated by mincing tumor specimens and culturing eluted lymphocytes with high doses of IL-2. TIL lines can be expanded to $10^8$–$10^{11}$ cells over 3–8 weeks in culture, and some lines appear to function as T cells with lytic specificity for autologous but not allogeneic tumor targets, whereas others function as LAK cells and lyse both autologous and allogeneic tumor targets (Topalian et al., *J. Immunol. Methods* 102:127, 1987; Itoh et al., *Cancer Res.* 46:3011, 1986). Adoptive transfer of $5 \times 10^{10}$ TIL alone has not been associated with significant toxicity (Kradin et al., *Cancer Immunol. Immunother.* 24:76, 1987), and administration of $5 \times 10^{10}$ TIL cells with concurrent systemic IL-2 has resulted in only toxicities attributable to the IL-2 (Rosenberg et al., *N. Engl. J. Med.* 319:1676, 1988; Topalian et al., *J. Clin. Oncol.* 6:839, 1988). Evaluation of the migration patterns of transferred TIL cells by infusion of indium-111 labeled cells has revealed initial localization of TIL cells in the lungs, liver and spleen at 2 hours after intravenous infusion, followed by emigration and preferential localization at sites of metastatic tumor by 24 hours (Fisher et al., *J. Clin. Oncol.* 7:250, 1989). Partial and complete tumor regressions have been seen in patients following a single TIL cell infusion, demonstrating these long-term cultured immune effector cells can mediate in vivo biologic effects.

Recently, TIL from several different individuals have been transduced to express resistance to toxic doses of G418 by introduction of the neomycin phosphotransferase gene with retroviral-mediated gene transfer (Kasid et al., *Proc. Natl. Acad. Sci. USA* 87:473, 1990). These TIL have been administered to cancer patients and the expression of the marker gene encoding neomycin phosphotransferase used to determine in vivo persistence and distribution. Preliminary data from these studies have demonstrated the localization of TIL cells at tumor sites long after transfer and illustrate the feasibility and safety of using retrovirally-mediated gene transfer to mark human T cells (Miller, *Human Gene Therapy* 1:5, 1990; Rosenberg et al., *N. Eng. J. Med.* 323:570, 1990).

Culture systems have now been developed in which human virus-specific $CD8^+$ CTL can be cloned and expanded in vitro (Riddel and Greenberg, *J. Immunol. Meth.* 128:189, 1990). These CTL maintain specificity for viral antigens after more than one year in culture, can be stimulated to proliferate with either virally-infected cells or antibodies to the CD3 complex of the T cell receptor, and can survive in vitro for prolonged periods without stimulation if placed on filler cells. Such in vitro generated cells specific for viral or tumor antigens could be used for adoptive immunotherapy.

The following examples illustrate specific embodiments of the present invention and are not intended to limit the scope of the invention as defined in the claims.

EXAMPLES

Example 1

Construction and Production of IL-1 R Retrovirus

A. Vector Construction.

The full-length cDNA encoding the type I murine IL-1 receptor from clone 78 (Sims et al., *Science* 241:585, 1988) was inserted as an EcoRI-SalI fragment between the EcoRI and XhoI sites of the retroviral vector pLXSN (Miller and Rosman, *Biotechniques* 7:980, 1989). The pLXSN retroviral vector is shown in FIG. 1 with the murine IL-1 receptor eDNA insert. The pLXSN retrovital vector consists of the 5' LTR and sequences through base 541 from MoMSV, bases 566 to 1038 from MoMLV, non-retroviral sequences, and base 7774 through the 3' LTR from MoMLV. The stippled box represents the SV40 sequences from a Pvu II to Hind III fragment from SV40 containing the early promoter (Fiers et al., *Nature* 273:113, 1978; Reddy et al., *Science* 200:494, 1978). The neo sequences are derived from transposon Tn5 (Beck et al., *Gene* 19:327, 1982). The resulting vector, termed pL.IL-1RSN, shown in FIG. 1, expresses the murine IL-1R cDNA under the transcriptional control of the retroviral LTR and the neogene under the control of the SV40 early region promoter. The neo gene is used as a positive selectable marker.

B. Production of Virus-producing Clone.

The L.IL-1RSN retrovirus was produced by a single clone of infected $\psi 2$ cells, which was derived as follows. The pL.IL-1RSN plasmid DNA was transfected into $\psi 2$ cells using the calcium phosphate procedure as previously described (Overell et al., *Molec. Cell. Biol.* 7:3394, 1987) and virus supernatant harvested 24 hours after transfection. Virus supernatants were routinely centrifuged (2500 rpm in a benchtop centrifuge for 10 minutes) to remove viable virus-producing cells. This supernatant was then used to infect fresh $\psi 2$ cells for 3 h in the presence of 4 µg/ml polybrene and 5 µg/ml tunicamycin. The recipient $\psi 2$ cells had been pretreated with tunicamycin for 4 h to allow infection by the ecotropic virus. These infected cells were grown for a further 24 h and then replated in medium containing G418 (500 µg/ml). Clones of G418-resistant cells were isolated using cloning tings, amplified in number and titered as previously described (Overell et al., *Molec. Cell. Biol.* 7:3394, 1987). The clones were also assayed for the presence of helper virus using the the XC/UV plaque assay (described in Weiss et al. (eds.) RNA *Tumor Viruses*, 2nd Ed., Vol. 1 (Cold Spring Harbor Laboratory, New York, 1985, pp. 209–260). Of several high-titer clones obtained, one clone, designated L.IL-1RSN-$\psi$2t6, was selected for further use. This clone had a virus titer of $5 \times 10^6$ $G418^R$ CFU/ml and was free of detectable helper virus as determined by the XC/UV plaque assay.

Example 2

Characterization. Of th L.IL-1RSN retrovirus

A. Determination of proviral structure in producer $\psi 2$ cells.

Figure 2:
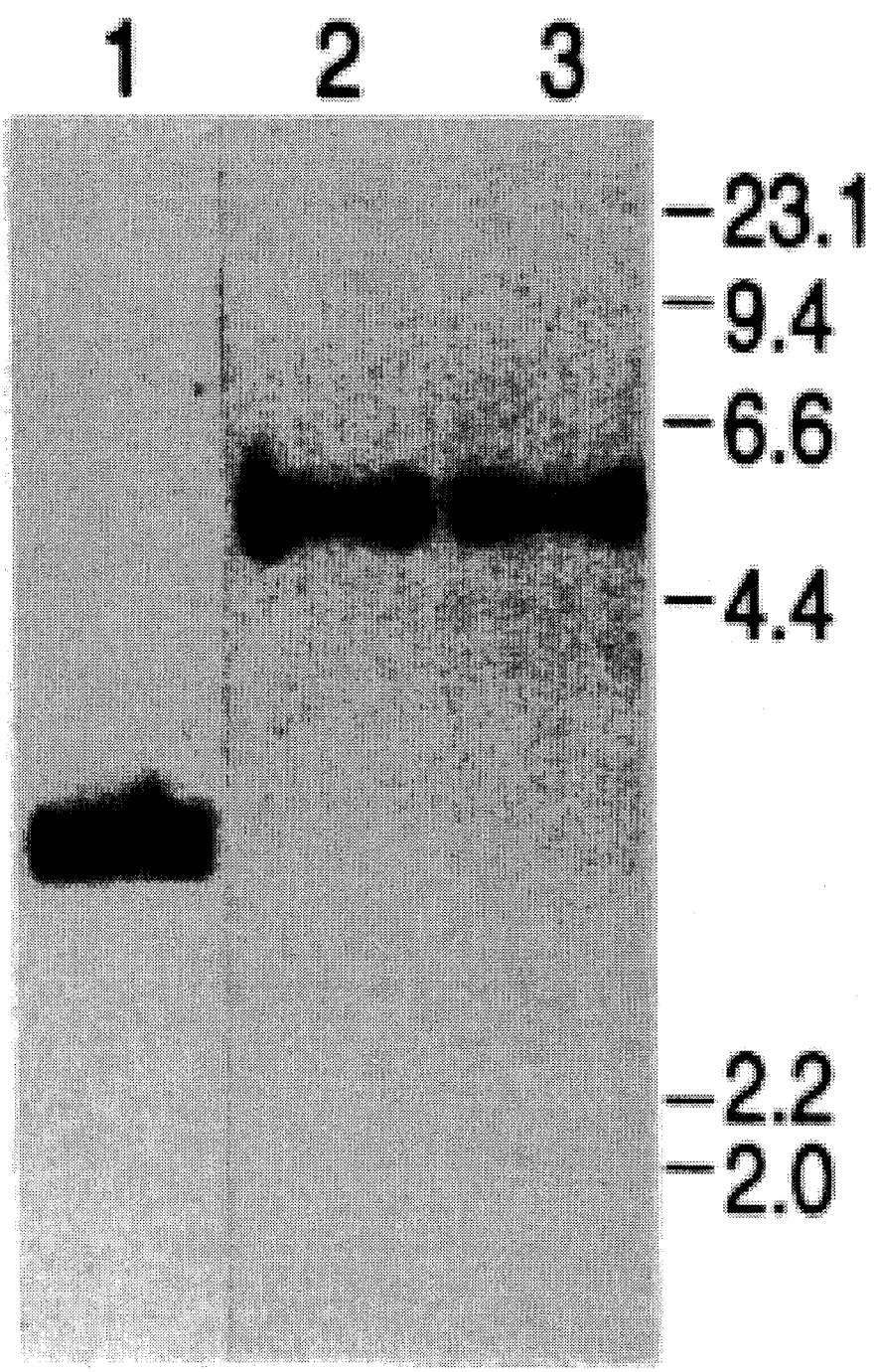
FIG. 2 shows the results of Southern analysis of the L.IL-1RSN provirus in the infected ψ2 producer cells. Genomic DNA from the L.IL-1RSNψ2t6 virus-producing clone was digested with BamHI (lane 1) or EcoRV (lane 2). The pL.IL-1RSN plasmid DNA was digested with EcoRV (lane 3) as a positive control for the expected size of the integrated provirus. All digests were run on a gel and blotted to nitrocellulose. The blot was then hybridized with a radiolabeled neo-specific probe. The single band in lane 1 indicates that the virus producing clone contained a single copy of the integrated vector provirus (since each proviral integrant would have a unique and different sized BamHI fragment). The same sized bands excised from the L.IL-1RSNψ2t6 virus-producing clone (lane 2) and from the pL.IL-1RSN plasmid (lane 3) following EcoRI digestion, demonstrates that the L.IL-1RSN provirus was integrated in an unrearranged form in the virus-producing clone.

The structure of the L.IL-1RSN provirus in the infected $\psi 2$ producer cells was determined by Southern analysis. Digestion of the genomic DNA with BamHI and hybridization with a radiolabeled neo-specific probe revealed a single hybridizing band (FIG. 2, lane 1). Since this fragment represented the junction fragment flanking the provirus (see FIG. 1) and would be different for each proviral integrant, this indicated that the virus-producing clone contained a single copy of the integrated vector provirus. Digestion of genomic DNA from the L.IL-1RSN-$\psi 2$ cells with EcoRV released a vector fragment of the expected size (FIG. 1) which hybridized with a probe specific for the neo gene (FIG. 2, lane 2) and was of the same size as the fragment released from the pL.IL-1RSN plasmid DNA by EcoRV digestion (FIG. 2, lane 3), indicating that the L.IL-1RSN integrated provirus was present in unrearranged form in the producer clone.

B. Characterization of IL-1R Protein Expressed by L.IL-1RSN Retrovirus.

Expression of the mIL-1R protein encoded by the vector was analyzed in infected WI26-VA4 human fibroblasts (ATCC CCL95.1) using a monoclonal antibody, M5, specific for the type I murine IL-1R (Bomsztyk et al., *Proc. Natl. Acad. Sci. (U.S.A.)* 86:8034, 1989). The type I murine IL-1R was expressed in human cells because murine cell lines express endogenous IL-1R which would have made analysis of the introduced receptor equivocal. As a negative control, WI26-VA4 cells were infected with the LXSN virus which confers expression of G418 resistance but does not contain the IL-1R cDNA.

Amphotropic virus stocks of L.IL-1RSN were generated by infecting the amphotropic PA317 packaging cell line (Miller and Buttimore, *Mol. Cell. Biol.* 6:2895, 1986; ATCC CRL 9078; U.S. Pat. No. 4,861,719) with supernatant from the L.IL-1R-$\psi$2t6 cell line. Amphotropic stocks of LXSN were obtained by infecting PA317 cells with supernatant from $\psi 2$ cells transiently expressing the LXSN vector following transfection as described above. The PA317 cells were seeded at a density of $5 \times 10^5/100$ mm culture dish and 24 hours later the ecotropic viral supernatants were added in the presence of 4 µg/ml polybrene. These viral supernatants were replaced with fresh culture medium and viral supernatant harvested after 3 days of incubation. The WI26-VA4 cells, seeded 24 h earlier at a density of $10^5$ cells in replicate 100 mm culture dishes, were infected with serial dilutions of LXSN or the L.IL-1RSN viral supernatants from PA317 cells. These cells were selected in situ in with G418 (1 mg/ml) and after 14 days growth the resulting colonies were incubated with $^{125}$I-M5 to visualize expression of the mouse IL-1R by autoradiography and stained with methylene blue to visualize all viable colonies of cells.

Figure 3:
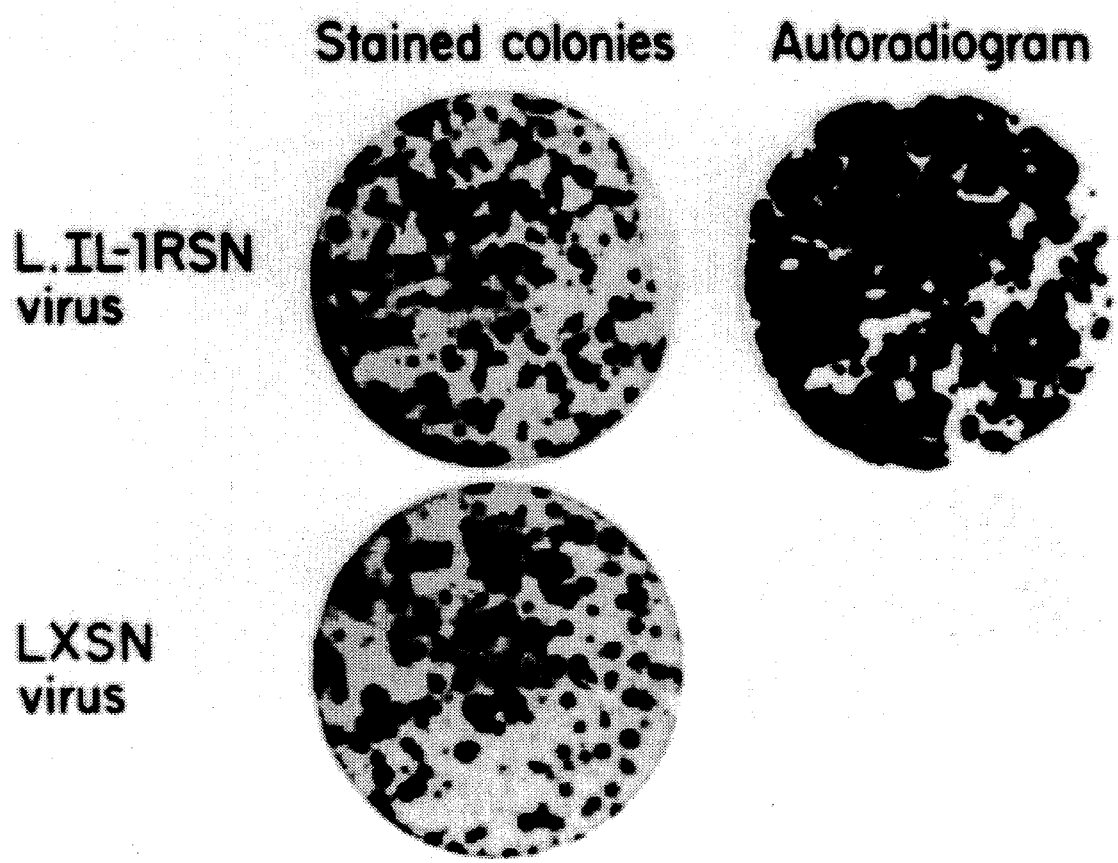
FIG. 3 compares autoradiogram and stained colonies of cells infected with the LXSN virus or with the IL-1R expressing virus. Colonies infected with retroviral vector L.IL-1RSN (expressing murine type I IL-1R) and colonies infected with a control vector LXSN (not expressing IL-1R) were stained with methylene blue to visualize all viable colonies of cells. The stained colonies show roughly equal numbers of cells on the LXSN and L.IL-1RSN plates. The autoradiogram represents colonies bound with anti-IL-1R $^{125}$I-M5 antibody and exposed to film. Dark spots on the film indicate that anti-IL-1R $^{125}$I-M5 antibody binds to IL-1R. The dark spots on the autoradiogram of the colonies derived following infection with L.IL-1RSN indicate that anti-IL-1R $^{125}$I-M5 antibody has bound to IL-1R expressed on the cell surface. In contrast, the complete absence of any dark spots on the autoradiogram of the LXSN control vector indicate the absence of cell surface IL-1R.

Comparison of the autoradiogram and the stained colonies (FIG. 3) indicated that the colonies derived from infection with the IL-1R virus bound the M5 antibody, while those derived from infection with the LXSN virus did not. Since all of the $G418^R$ colonies derived following infection with L.IL-1RSN bound IL-1, this experiment also showed that selection in G418 led to coexpression of the IL-1R.

Figure 4:
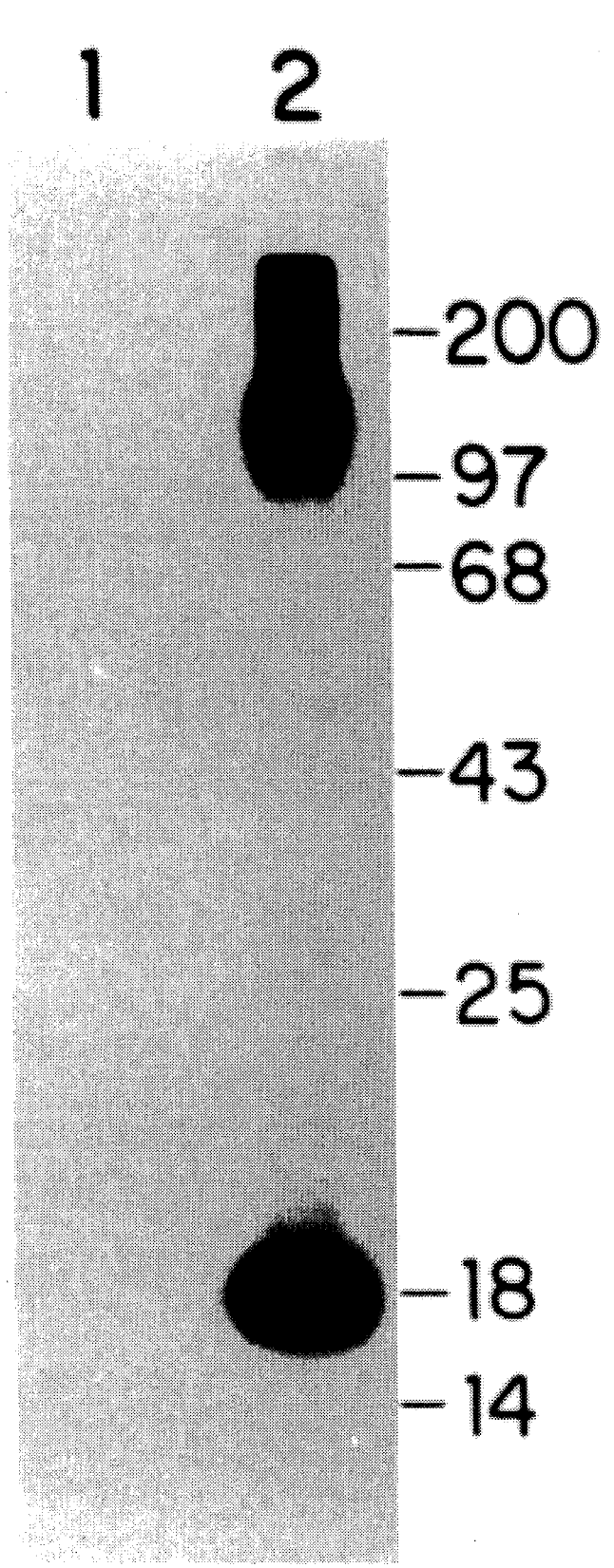
FIG. 4 shows the results of cross-linking studies in which WI26-VA4 cells infected with L.IL-1RSN (expressing murine type I IL-1R) were bound to murine $^{125}$I-IL-1, which was then cross-linked to the IL-1R using disuccinimidyl suberate (DSS). The cross-linked material was then precipitated using an anti-IL-1R monoclonal antibody bound to affigel, and then analyzed by SDS-PAGE and autoradiography. The 97 kD band in lane 2 is consistent with a type I murine IL-1R/IL-1 complex. The approximately 18 kD band represents free $^{125}$I-IL-1. Lane 1, from cells infected with the negative control vector LXSN, show no cross-linked material.

To analyze the size of the transduced IL-1R, $G418^R$ colonies from parallel plates of infected WI26-VA4 cells from the above experiment were pooled, grown up in G418 and the resulting cells bound with $^{125}$I-IL-1$\alpha$, which was then cross-linked to the receptor with 1 mg/ml disuccinimidyl suberate (DSS; Dower et al., *J. Exp. Med.* 162:501, 1985). The cells were then extracted with 1% Triton X-100 and incubated with the M5 antibody bound to affigel. The bound material was eluted and analyzed by SDS-PAGE and autoradiography. The results of this experiment are shown in FIG. 4, which is an autoradiogram showing a cross-linked band migrating at a molecular weight consistent with the type I murine IL-1R/IL-1 complex (97 kD; Dower et al., *J. Exp. Med.* 162:501, 1985). This band was present in lanes containing M5 antibody purified extracts from cells infected with L.IL-1RSN (lane 2) but not from cells infected with the negative control LXSN vector (lane 1). This data demonstrates that the L.IL-1RSN vector transmitted expression of authentic murine IL-1R by retroviral infection.

Example 3

Figure 5:
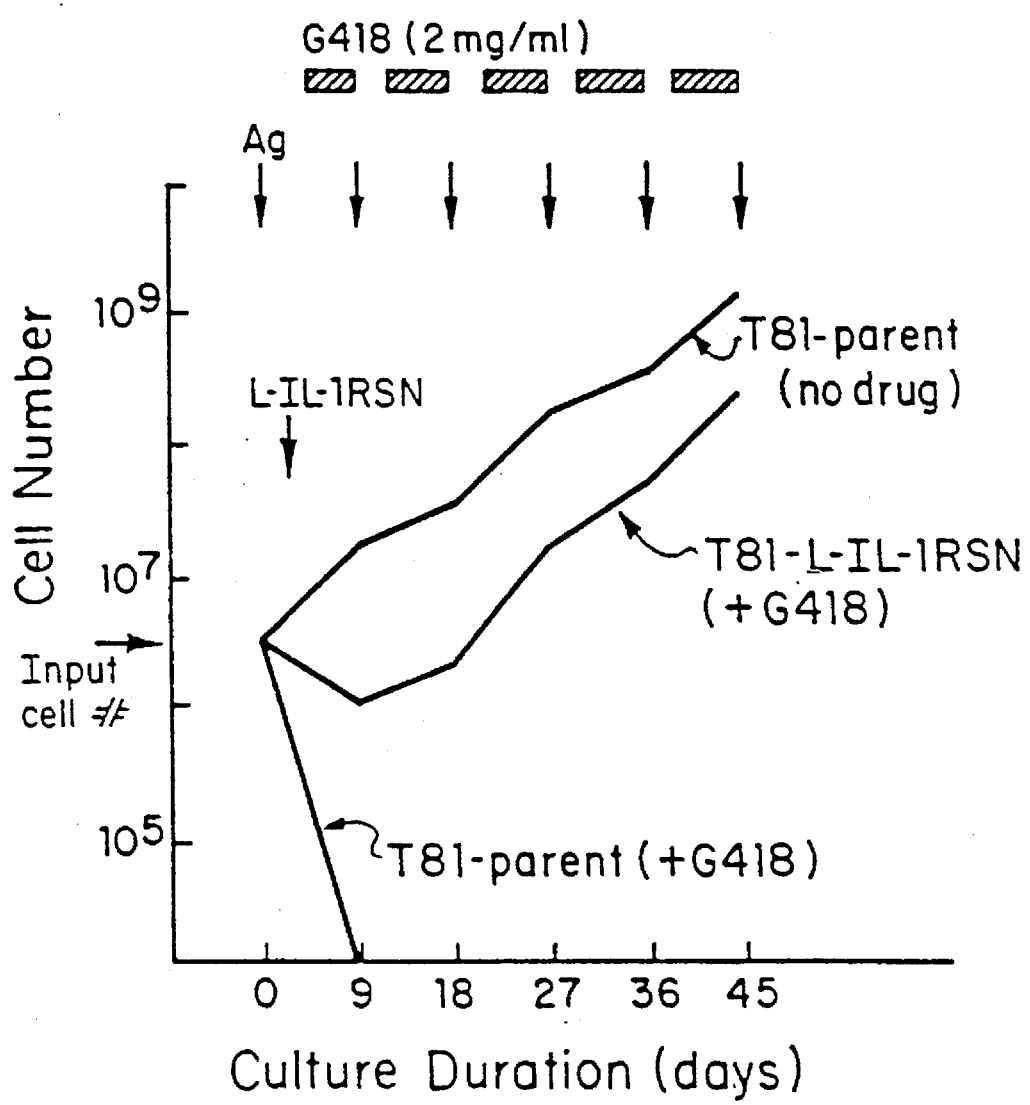
FIG. 5 is a graph comparing the outgrowth of CTL cells in the antibiotic G418 following infection with IL-1R retrovirus to growth of the parental cell line in the presence and absence of G418. The CD8$^+$ CTL clone T81 was infected with supernatant from L.IL-1RSNψ2t6 cells producing the L.IL-1RSN retrovirus) and selected in G418. The graph shows that G418 was toxic to the parental cells, causing a decline in cell number. Cells not selected in G418 steadily increased in number. The cells infected with L.IL-1RSN showed an initial decline in cell number, followed by growth parallel with that of the parental clone in the absence of drug selection.

Genetic conversion of cytotoxic T lymphocytes to a helper-independent phenotype by introduction of an IL-1 recentor cDNA A. Selection of CD8$^+$ T Cell clone T81 transduced with retroviral vector L.IL-1RSN encoding murine IL-1R. The retroviral vector L.IL-1RSN encoding the murine IL-1 receptor was introduced into the tumor specific CD3$^+$, CD8$^+$ T cell clone T81 as follows. T81 is specific for an antigen expressed on the K1735 mouse melanoma cell line. T81 was propagated by stimulation every 8–10 days with tumor antigert and irradiated syngeneic splenocytes as feeder cells. Recombinant IL-2 (50 U/ml) was added to the cultures 48 hours following stimulation. To transduce the T cell clones, supernatant containing retroviral particles from the L.IL-1RSNψ2t6 cell line were added in a 1:1 dilution 48 hours after stimulation and drug selection (G418) was begun 2 days later. G418 was subsequently added 2 days following each stimulation to select T cells that stably expressed G418 resistance. The graph shown in FIG. 5 shows that the doses of G418 used were toxic to the parental cells, and that after an initial decline in cell number, the growth of transduced cells (T81-IL-1R) in the presence of drug selection paralleled the growth of the parental clone in the absence of drug selection.

B. Cell surface expression of recombinant murine type I IL-1R on CD8$^+$ T cell clone T81.

Figure 6:
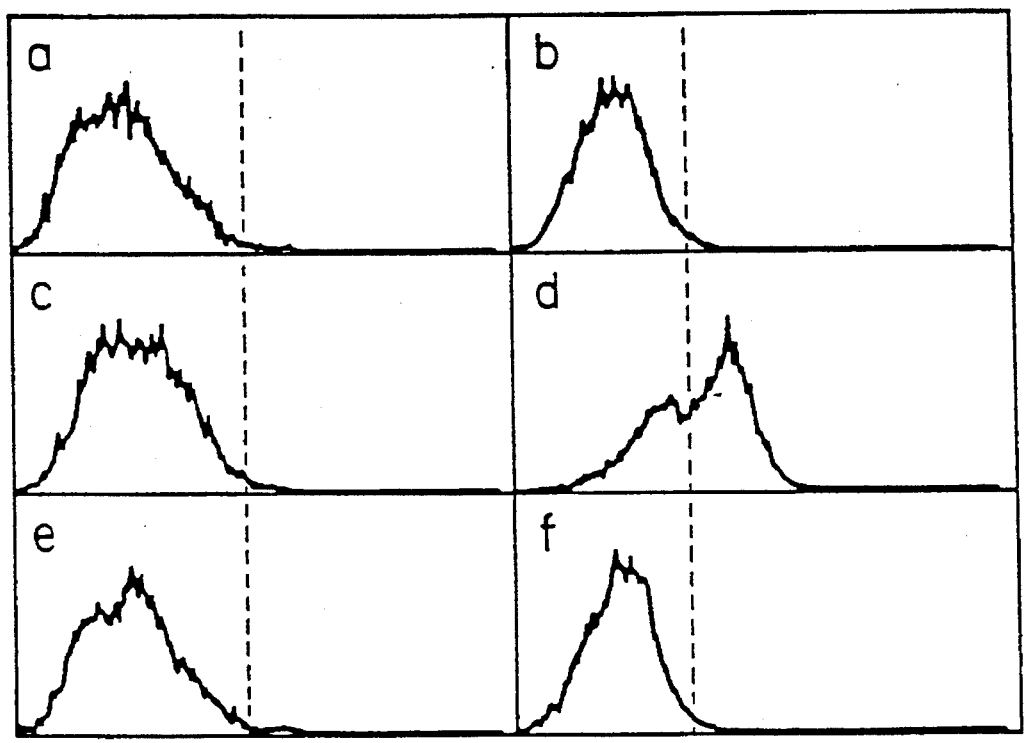
FIG. 6 shows analysis of cell surface expression of IL-1 receptor on transduced T81 CTL by flow cytometry (stained with phycoerythrin-M5 monoclonal antibody conjugates). Panels (a), (c) and (e) show results from experiments using parental T81 cells and panels (b), (d), and (f) show results from experiments using T81 cells transduced with IL-1 receptor (T81-IL-1R). Panels (a) and (b) are with cells alone, panels (c) and (d) are with cells stained with phycoerythrin linked to anti-IL-1R monoclonal antibody M5 (PE-M5) and panels (e) and (f) are with cells stained with PE-M5 in the presence of a 50-fold excess of unconjugated M5 as competitor. The absence of a shift in fluorescence in panel (c) relative to panel (a) shows that the parental T81 cells do not have detectable cell surface IL-1 receptors. The presence of a shift in fluorescence in panel (d), on the other hand, shows that cell surface IL-1 receptors are present on the T81-IL-1R cells.

Transducer and parental T81 T cells were suspended at $10^6$ cells/ml and stained with 10 µg/ml of a conjugate of the M5 monoclonal antibody (specific for the murine type I IL-1R) directly coupled to phycoerythrin (PE-M5). The cells were analyzed for M5 binding on a Beckton-Dickinson FACscan analyzer. The results shown in FIG. 6 demonstrate that the T81 cells infected with the mIL-1R retrovirus expressed readily detectable M5 binding, while the parental uninfected T81 cells did not (FIG. 6, a–d). The binding of M5 was completely reversible by competition with a 50-fold excess of unlabeled M5 antibody, indicating that the binding was specific (FIG. 6, e and f). Panel d shows the positive staining of transduced T81 cells with PE-M5 conjugate which is inhibited by unconjugated M5 (panel f). The results demonstrate that CD8$^+$ T cell clone T81 transduced with L-IL-1RSN expressed cell surface IL-1R.

C. Scatchard analysis.

Figure 7:
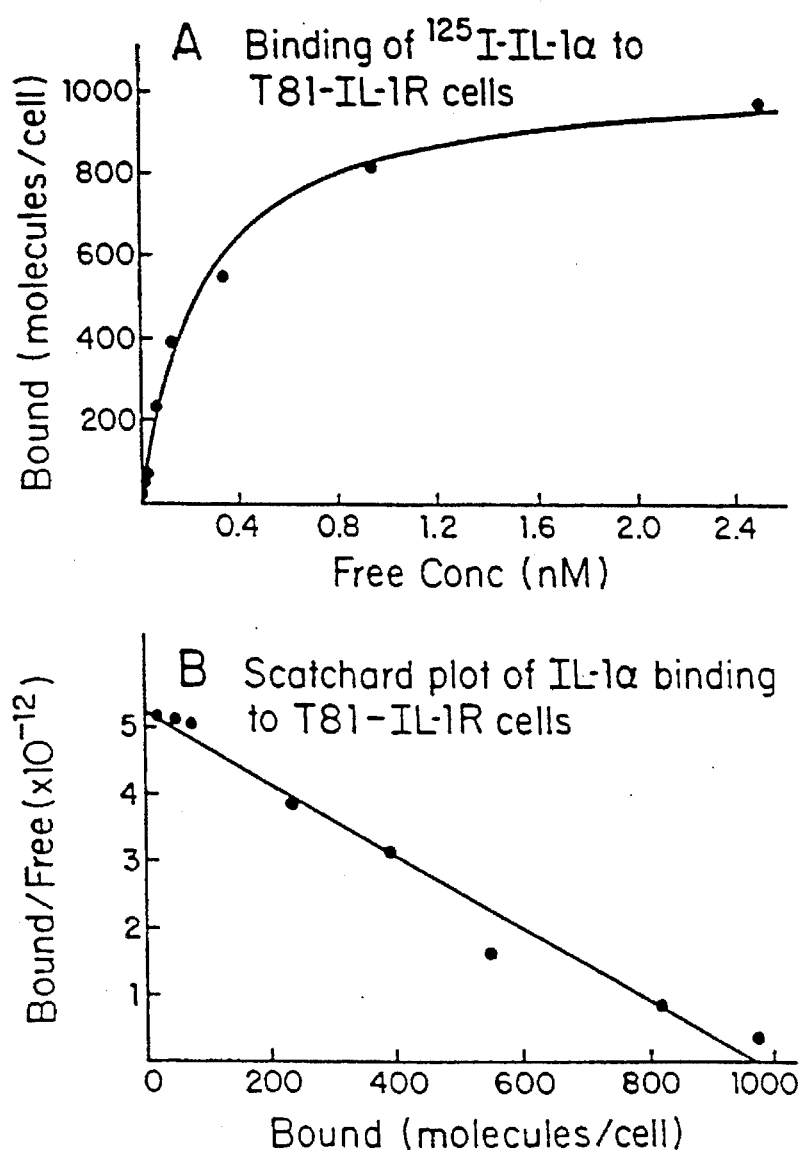
FIG. 7 shows binding of radiolabeled IL-1 to T81-IL-1R cells. Panel A shows direct binding of $^{125}I$ labelled recombinant IL-1α to T81-IL-1R cells. Panel B shows data corresponding to panel A replotted in the Scatchard coordinate system. This analysis demonstrates the presence of approximately 1000 high affinity IL-1 receptors/cell on clone T81-IL-1R.

The IL-1 receptors on the T81 cells infected with the L.IL-1RSN vector were analyzed for $^{125}$I-IL-1α binding as previously described (Dower et al., Nature (Lond) 324:266, 1986). Panel A of FIG. 7 shows direct binding of $^{125}$I labelled recombinant IL-1α to IL-1R bearing T81 cells. T cells were incubated in the presence of various concentrations of $^{125}$I-IL-1α for 24 hours at 8° C. on a rocker platform. Nonspecific binding of $^{125}$I-IL-1 was measured by incubation in the presence of an excess of unlabelled IL-1. At the end of the incubation, bound and free $^{125}$I-IL-1 were separated by centrifugation over a phthalate oil mixture and the amount of radiolabel in each fraction measured. The data were corrected for non-specific binding and then analyzed by nonlinear least square fitting to estimate the number of IL-1R/cell. Panel B shows the data from panel A replotted in the Scatchard coordinate system. This data indicate that the cells expressed an average of 980 receptors with a single affinity class with a $K_a$ of 5 nM$^{-1}$. This affinity is typical for the cloned type I murine IL-1R (Sims et al., Science 241:585, 1988).

D. Proliferative response of T81 cells expressing the IL-1R.

The T81 parental cells and their derivatives infected with L.IL-1RSN and expressing cell surface IL-1R were assayed for their ability to proliferate in response to various stimuli, including media, antigen presenting cells (APC), IL-1, tumor antigen (Ag), and combinations of Ag and APC, IL-1 and IL-2. The parental clone T81, and the T81 clone transduced with the retroviral vector L.IL-1RSN (and expressing murine IL-1R) were stimulated in triplicate cultures in 96 well plates ($5\times10^4$ T cells/well) with the various combinations of UV-irradiated antigen bearing tumor cells ($2\times10^4$ cells/well), irradiated syngeneic splenocytes as APC ($5\times10^5$ cells/well), IL-1 (10 ng/ml), or IL-2 (50 U/ml). Wells were pulsed with 1 µCi of $^3$H thymidine for the final 18 hours of a 72 hour assay and then harvested for β counting.

Figure 8:
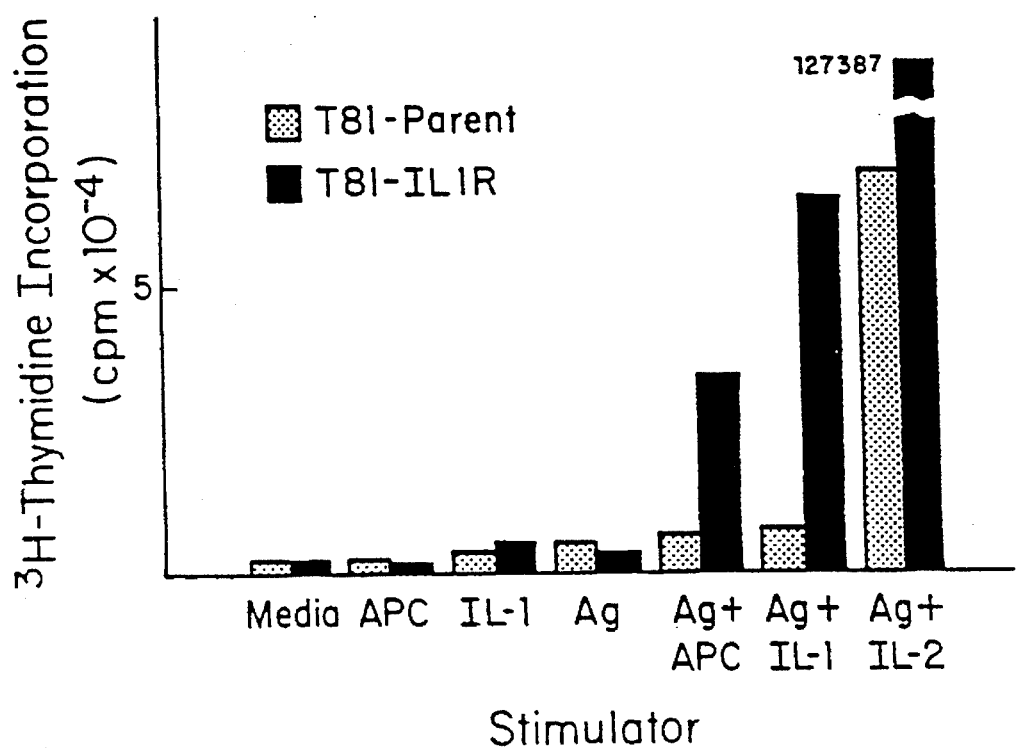
FIG. 8 shows the results of experiments in which murine T81 parental cells and their derivatives infected with the retroviral vector L.IL-1RSN (expressing cell surface IL-1R) were assayed for their ability to proliferate in the presence of various stimuli. Both parental and infected cells (expressing the IL-1R) proliferated in response to the combination of tumor antigen (Ag) and IL-2. In contrast to the parental cells, the cells infected with L.IL-1RSN were able to proliferate in response to the combination of Ag and antigen presenting cells (APC), or Ag and IL-1. This data demonstrates that CTL transduced with IL-1R proliferate in response to IL-1 and antigen presentation independent of $T_H$ cells or the cytokines they produce.

This data (shown graphically in FIG. 8) demonstrates that the parental T81 cells will not proliferate significantly in the presence of tumor antigen and APC or IL-1, but will proliferate in response to tumor antigen if exogenous IL-2 is provided. By contrast, the T8 1 cells infected with the IL-1R retrovirus (and expressing IL-1R) were able to proliferate in the presence of tumor antigen in the absence of IL-2 if IL-1 or APC were provided.

Example 4

Transfer of IL-1 Receptor Into Human CTL

A. Proliferative response of human CTL 3G5 and 3G5-IL-1R cells.

Figure 9:
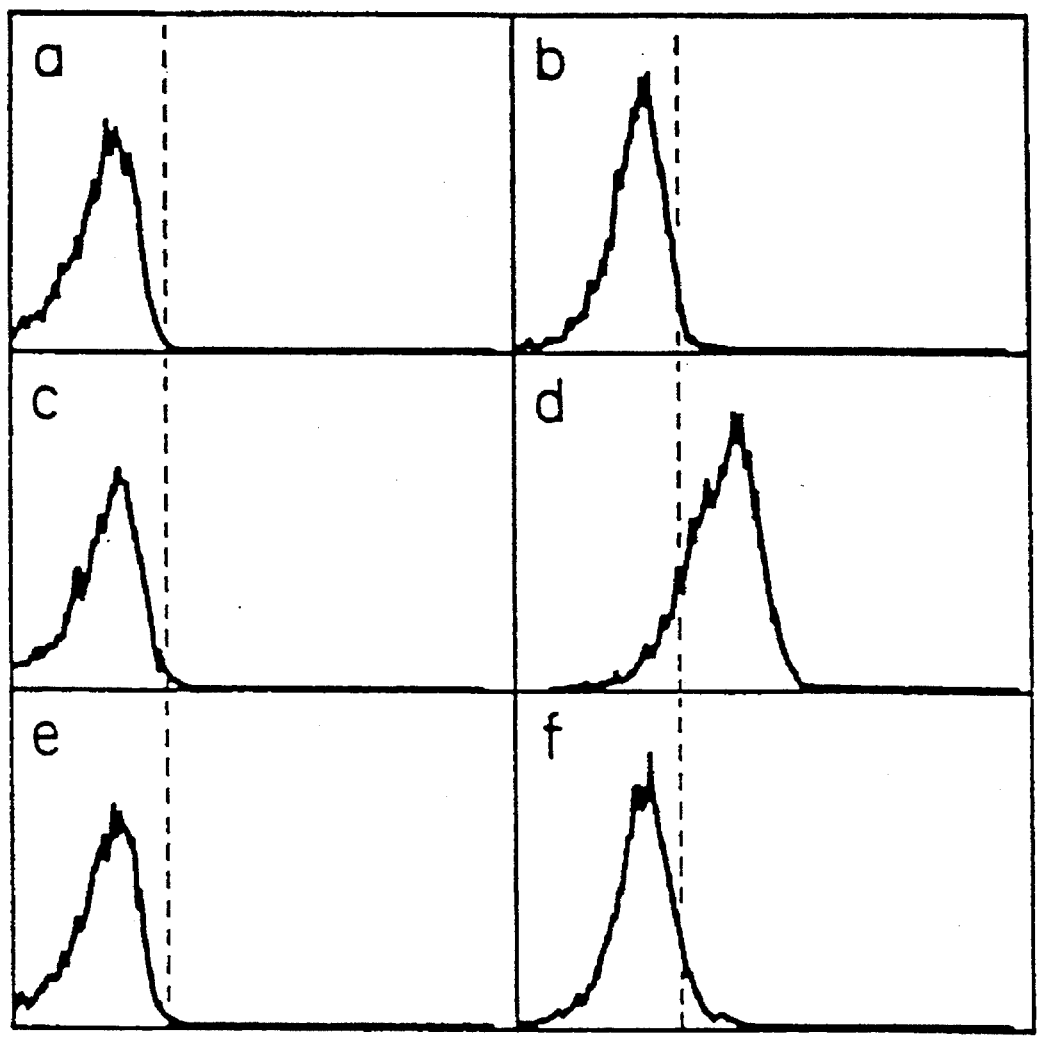
FIG. 9 shows results of cell surface expression of IL-1 receptor on transduced human CTL cells by flow cytometry (stained with phycoerythrin-M5 monoclonal antibody conjugates, PE-M5). Panels (a), (c) and (e) show results from experiments using parental 3G5 cells and panels (b), (d), and (f) show results from experiments using 3G5 cells transduced with IL-1 receptor (3G5-IL-1R). Panels (a) and (b) are with cells alone, panels (c) and (d) are with cells stained with PE-M5 and panels (e) and (f) are with cells stained with PE-M5 in the presence of a 50-fold excess of unconjugated M5 as competitor. The absence of a shift in fluorescence in panel (c) relative to panel (a) indicates that the cells do not express cell surface IL-1 receptor. The presence of a shift in fluorescence in panel (d), on the other hand, indicates that mouse IL-1 receptors are present on the surface of the 3G5-IL-1R cells.

Further experiments were carded out to assess the generality of the results obtained above to other CTL clones and in particular to see whether human CTL expressing a transferred ILo 1R would display a similar phenotype. A CD3$^+$, CD8$^+$ human alloreactive CTL clone, 3G5, is alloreactive to HLA-A2, and allogeneic HLA-A2(+) lymphoblastoid cell lines (LCLs) served as a source of antigen. The 3G5 clone was transduced with an amphotropic pseudotype of L.IL-1RSN, derived as described in Example 2 above, and the cells selected in G418. The resulting G418$^r$ cells (3G5-IL-1R) displayed specific binding of the M5 antibody by flow cytometry (FIG. 9, panel d) which was competed with a 50-fold excess of unconjugated M5 (FIG. 9, panel f). No binding of M5 was observed to the untreated cells (panels a and b) or to the M5-PE treated untransduced parental 3G5 cells (panel c). Since the M5 antibody is specific for the mouse IL-1R, this experiment showed that it was the transferred receptor that was being expressed.

The 3G5 and 3G5-IL-1R cells were assayed for their ability to proliferate in response to a variety of stimuli by seeding $5\times10^4$ 3G5 or the transduced 3G5-IL-1R cells in 96-well round bottom trays under various stimulator conditions. Autologous LCL (A2(−)LCL) cells served as an autologous stimulator, while A2(+)LCLs served as an allogeneic stimulator; these cells were added at a 1: 1 ratio to the responder cells. Human IL-1 and IL-2 were added at 10 ng/ml and 20 U/ml respectively. The cells were grown for 96 hr and pulsed with $^3$H-TdR for the final 18 hr of the assay. Wells were then harvested and thymidine incorporation assessed by beta scintillation counting.

Figure 10:
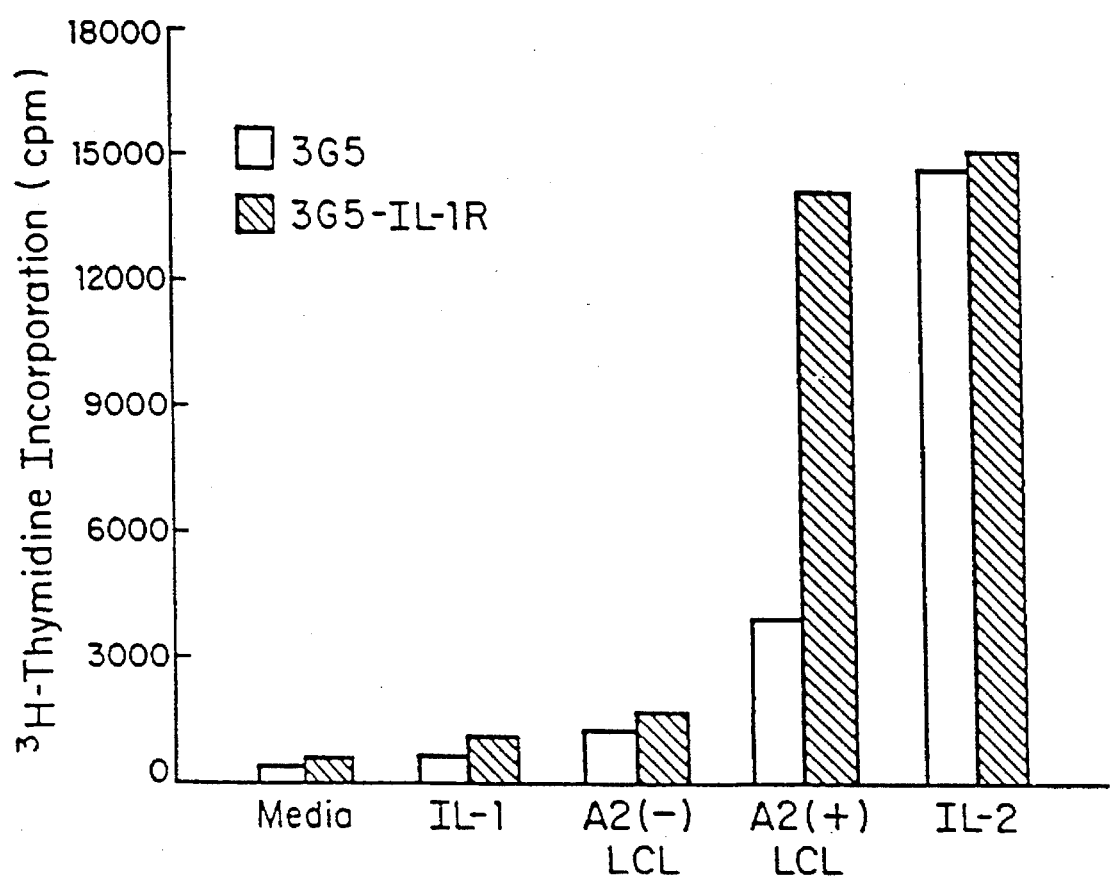
FIG. 10 shows the ability of human 3G5 parental cells and transduced 3G5-IL-1R cells to proliferate in the presence of various stimuli. Cells infected with the IL-1R retrovirus were able to proliferate in the presence of antigen presenting cells (A2$^+$ LCL). The parental cells were unable to proliferate equivalently under the same conditions. This data indicates that human CTL cells transformed with IL-1R proliferate in response to antigen presentation independent of $T_H$ cells.

In agreement with the data obtained above in the mouse system, the infected cells proliferated independently of a source of CD4$^+$ T cell-derived cytokines (FIG. 10). In this system, proliferation of the IL-1R⁺ cells could be achieved with the antigen-presenting cells alone (A2+LCL), probably because these cells make adequate levels of IL-1 to synergise with antigen and generate a response. The parental cells were unable to proliferate equivalently under the same assay conditions. The proliferation of 3G5-IL-1R was antigen dependent, since autologous A2(–) LCLs did not induce a proliferative response (FIG. 10).

Figure 11:
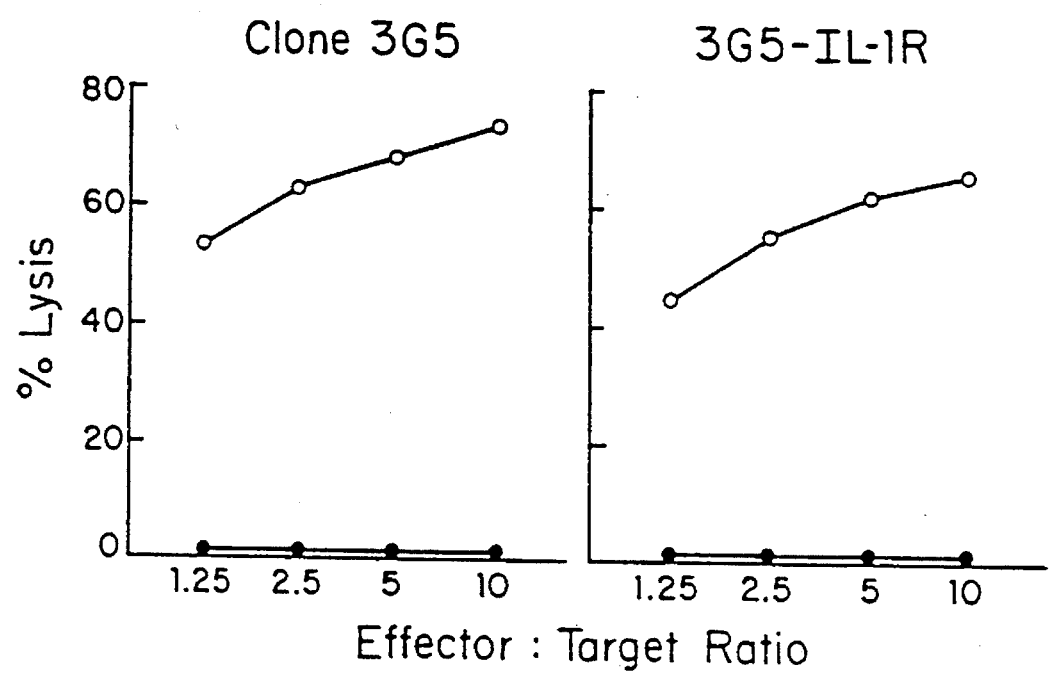
FIG. 11 shows the cytolytic reactivity of clone 3G5 and 3G5-IL-1R in a chromium release assay. Target cells were autologous (●) and HLA A2 positive allogenic EBV-LCL (○). Effector cells 3G5 and 3G5-IL-1R were added to achieve various effector to target cell ratios (x axis). The data shows that the alloreactive HLA A2-specific CD8$^+$ T cell clone 3G5 retains antigen-specific cytolytic reactivity following introduction and expression of the IL-1R.

The cytolytic reactivity of human clones 3G5 and 3G5-IL-1R were also evaluated in a 4 hour chromium release assay, substantially as described by Brunner et al., *Immunol.* 14:181, 1968. The target cells were autologous (●) and HLA-A2-positive allogenic EBVLCL (o). These cells were labelled for 90 minutes with 200 µCi of $^{51}$Cr, washed and plated in 96 cell round bottom plates at $5 \times 10^3$ cells/well. Effector cells 3G5 and 3G5-IL-1R were added to achieve various effector to target cell ratios (x axis) and the plates were incubated for 4 hours. Supernatants were harvested from experimental wells and from wells containing target cells and media alone to determine spontaneous release, or with NP-40 to determine normal release of $^{51}$Cr. The data shows that the alloreactive HLA A2-specific CD8⁺ T cell clone 3G5 retains antigen-specific cytolytic reactivity following introduction and expression of the IL-1R. The cells retained the ability to lyse the appropriate target cells, and retained their antigen specificity, in that no significant lysis of autologous, non-antigen-bearing cells was observed over a range of effector:target cell ratios (FIG. 11).

The results described above in Examples 1–4 indicate that insertion of the IL-1R renders CTL independent of their requirement for help from cytokines produced by CD4⁺ T cells. This result was obtained in both the mouse and the human systems, and based on these in vitro results it would be predicted that the IL-1R transduced cells would exhibit the ability to proliferate in vivo independently of T cell help. They would still, however, require antigen and IL-1 for proliferation, based on the above data. These results are of particular significance in the context of AIDS, since the deficiency of CD4⁺ helper T cells could be expected to prevent persistence of engrafted CD8⁺ CTL in vivo.

Example 5

Generation and characterization of HIV-specific CTL and transduction with IL-1R for use in adoptive immunotherapy A. Reagents
1. Culture media and media supplements.

The culture media used is RPMI 1640 for T cell cultures and Dulbecco's media for propagating vaccinia-gag and vacciniaRT virus on BSC-40 cells and for propagating PA317 cells used to package the retroviral vector. All media are purchased in 1 liter bottles from Whittaker MA Bioproducts and meet current FDA guidelines for use in adoptive immunotherapy studies in humans. Supplements to the culture media include glutamine (Whittaker MA Bioproducts), human AB serum for the T cell cultures and fetal calf serum for the fibroblast cultures. Following the addition of media supplements, all culture media are filtered through a 0.2 micron cellulose acetate filter (Nalgene) and screened for bacterial, fungal and mycoplasma contamination prior to use in cell cultures.

2. Human AB Serum.

Human AB serum is required as a supplement to culture media to support optimal long-term in vitro T cell growth. The human AB serum is prepared from blood type AB⁺ volunteer donors. At each donation, an aliquot of serum from individual donors is screened for HIV serology, HTLV I serology, hepatitis serology, alanine aminotransferase and STS. Serum from donors not meeting the same requirements used to assess blood for transfusion is discarded. All serum is screened for bacterial, fungal and mycoplasma contamination and then pooled prior to use in culture media. Pooled serum is heat treated at 56° C. for 30 minutes to inactivate serum complement and potential viral contaminants and passed through a 0.2 micron cellulose acetate filter. Aliquots of pooled serum used in culture media are stored for at least 1 year in order that the serum can be investigated as a source should the recipients of immunotherapy with HIV-specific T cells develop hepatitis, mononucleosis or other viral illness.

3. Fetal calf serum (FCS).

FCS is added as a supplement to culture media used to grow the BSC-40 cell line, the PA317 packaging cell lines and autologous EBV-induced B cell lines. All FCS is purchased from Hyclone, screened for bacterial, fungal and mycoplasma contamination, heat inactivated at 56° C. for 30 minutes and filtered through a 0.2 micron filter prior to use in culture media. Fetal calf serum is not used in the media to grow human T cells for immunotherapy.

4. Interleukin 2.

Human recombinant Interleukin 2 (IL-2) is obtained from Hoffmann-La Roche. IL-2 is supplied in vials containing 0.67 mg of lyophilized IL-2 having a specific activity of $1.5 \times 10^6$ units/mg protein. Less than 0.04 ng of endotoxin is present per vial, as measured by Limulus amebocyte assay. This recombinant IL-2 has been used to generate human LAK cells in vitro for use in human cancer therapy and has been administered systemically to human cancer patients in phase I and II immunotherapy studies.

The lyophilized recombinant IL-2 is reconstituted with sterile water and diluted to a concentration of $5 \times 10^5$ units/ml. IL-2 is aliquoted into sterile vials and stored at –20° C. IL-2 is used in the T cell cultures as described below in Section C.

B. Culture of Human HIV-Specific T Cells for Adoptive Immunotherapy

1. Peripheral Blood Lymphocytes—Collection and Separation.

Peripheral blood lymphocytes (PBL) are obtained from the HIV-seropositive donor by venipuncture and isolated by Ficoll Hypaque density gradient centrifugation. PBL are washed twice in sterile phosphate buffered saline and suspended in culture media consisting of RPMI 1640, 10% human AB serum, and 4mM L glutamine. Mononuclear cells are used for initiation of T cell cultures, irradiated for use as filler cells, transformed with EBV to provide LCL as feeder cell lines, or stored for future use by freezing the cells in liquid nitrogen after suspension in RPMI with 20% human AB serum and 10% DMSO.

2. EBV-Induced B Cell Lines.

EBV-induced autologous B cell lines are generated from the HIV-seropositive donor and used as feeder cells to support in vitro T cell growth. EB V is obtained from filtered supernatants of the B95-8 cell line (American Type Culture Collection #CRL 1612). B-lymphoblastoid cell lines (B-LCL) are induced by culture of PBL with this supernatant in the presence of cyclosporine A, and subsequently propagated in RPMI 1640 with 10% FCS. All B-LCL are screened for mycoplasma, bacterial and fungal contamination prior to use as γ irradiated feeder cells and stimulator cells for T cell cultures.

3. Generation of CD8⁺ HIV-Specific $T_C$ Clones.

To determine if the seropositive donors have CTL specific for HIV gene products, PBL are assayed for lyric activity against vac/gag, vac/env, vac/reverse transcriptase (RT) and vac infected autologous and class I MHC mismatched LCL as described (Walker et al., *Proc. Natl. Acad. Sci. USA* 86:9514, 1989; Langlade-Lemoyen et al., *J. Immunol.* 141:1949, 1988; Riviere et al., *J. Virol.* 63:2270, 1989; Walker et al., *Science* 240:64, 1988). To generate CD8$^+$HIV-gag and RT specific CTL clones, $5\times10^6$ PBL obtained from the HIV seropositive donors are stimulated in sterile 6 well plates with $5\times10^5$ autologous B-LCL infected for 16 hours with vaccinia-gag or vaccinia-RT, respectively, at an MOI of 10 and subsequently inactivated with a germicidal UV light. These cultures are incubated at 37° C. and 5.5% $CO_2$ for 7 days and would be expected to activate and expand both EBV and HIV gag- and RT-specific T Cells. These cells are then isolated by T cell cloning. The CD8$^+$ T cells are enriched for cloning by depleting the cultures of CD4$^+$ T cells with OKT4 mAb and rabbit complement. The enriched CD8$^+$ T cells are cloned in 96 well round bottom plates at 0.3 T Cells/well with $5\times10^4$ autologous γ irradiated (33Gy) PBL/well as feeder cells, anti-CD3 mAb for stimulation and 50 U/ml recombinant IL-2. Wells positive for growth are identified after 7–10 days of culture and are screened in a microcytotoxicity assay 12–14 days following plating to identify those clones with lytic specificity for autologous vac/gag or vac/RT infected LCL but not vac-infected LCL or uninfected LCL. These HIV-specific T cell clones are transferred to larger wells and restimulated every 7–10 days with anti-CD3 mAb, autologous γ irradiated PBL and fed with 40 U/ml IL-2 48 and 96 hours after each restimulation. Twenty clones demonstrating rapid in vitro growth are selected for characterization, expansion, transduction with L.hIL-1RSN (see below) and for use in therapy. CD8$^+$ HIV-specific $T_C$ clones should expand 5–10 fold in cell number with each weekly stimulation. Thus, sufficient cell numbers should be available 8–12 weeks after cloning to begin adoptive therapy studies.

4. Characterization of HIV-Specific $T_C$ a) Cell Surface Phenotype.

Class I MHC-restricted $T_C$ should have a CD3$^+$, CD8$^+$, αβ$T_C$R$^+$, CD4$^-$, CD16$^-$ cell surface phenotype and an aliquot of all clones. is analyzed by indirect immunofluorescence using monoclonal antibodies OKT$_3$(CD3), Leu2a (CD8), WT/31 (αβ$T_C$R), OKT4 (CD4), and Leu11b (CD16) to confirm the expected phenotype.

b) Specificity for HIV gag or RT and Class I MHC Restricting Element.

CD8$^+$ $T_C$ recognize and lyse virally infected cells following interaction of the antigen-specific T cell receptor with processed viral antigen presented by class I MHC molecules of the infected cells. The requirements for gag or RT presentation and class I MHC restriction is confirmed by assaying each clone against autologous and class I MHC mismatched vac/gag or vac/RT infected and uninfected LCL. Blocking studies are done using the anti-class I mAb W6/32 as further conformation of class I MHC restriction.

C. Retroviral Mediated Gene Transfer into Human HIV-Specific T Cell Clones

1. Retroviral Vector.

The retroviral vector used in this study, L.hIL-1RSN is similar to the L.IL-1RSN vector (FIG. 1) except that is expresses the human type I IL-1R cDNA gene in place of the murine IL-1R cDNA. The L.hIL-1RSN vector is constructed by inserting the full length cDNA encoding the human IL-1R as described by Sims et al., *Proc. Natl. Acad. Sci. USA* 86:8946, 1989) as a SytI-BglII fragment into the HpaI site of LXSN. The L.hIL-1RSN retroviral vector is produced at high liter and free of helper virus using an infected clone of the PA317 packaging cell line (Miller and Buttimore, *Mol. Cell Biol.* 6:2895, 1986; ATCC CLR 9078; U.S. Pat. No. 4,861,719) as described in Examples 1 and 2.

2. Transduction of Human CD8$^+$ T Cell Clones by Retroviral Infection.

CD8$^+$ HIV-specific T cell clones are stimulated at $5\times10^5$/ml in 6 well plates or 75 cm$^2$ flasks with anti-CD3 mAb and irradiated feeder cells. Twenty-four hours after activation, IL-2 (50 U/ml) is added to the culture to induce T cell proliferation. Twenty-four hours following the addition of IL-2, the activated T cells are centrifuged and resuspended in a 1:1 (vol:vol) ratio of cell culture media with 50 U/ml IL-2 and cell culture supernatant containing the retroviral particles at a titre of $5\times10^6$ cfu/ml with polybrene 6 μg/ml. The T cell clone is allowed to proliferate in culture for 5 days, restimulated with anti-CD3 mAb and fed with media containing IL-2 (50 U/ml) and G418 at 2 mg/ml 48 hours after stimulation. These cells are then assayed for their ability to proliferate in the absence of $T_H$ function as described above in Example 4.

Infusion of autologous CTL containing the transduced IL-1R begins 8–12 weeks following the initiation of the T cell cultures and consists of three infusions of escalating doses of autologous CD8$^+$ HIV-specific T cell clones, given 3 weeks apart.

Each patient receives three intravenous T cell infusions at increasing cell doses given three weeks apart, according to the dose escalation scale outlined in Table 1.

TABLE I

HIV-specific CTL Administration - Dose Escalation

| Dose Level | Day | #CD8$^+$ T cells administered |
|---|---|---|
| 1 | 0 | $3 \times 10^7/m^2$ |
| 2 | 21 | $3 \times 10^8/m^2$ |
| 3 | 42 | $3 \times 10^9/m^2$ |

T cell clones to be administered are harvested from cultures, washed three times in 0.9% saline, pooled, and resuspended in 100–250 ml of 0.9% NaCl with 2% human AB serum. T cells are administered intravenously through a large bore needle over 30–60 minutes.

Example 6

Use of IL-1R Transduction to Augment the Effectiveness of TIL Immunotherapy

TIL have been used in both mice and humans for adoptive tumor immunotherapy. These cells are isolated and grown in culture according to the methods described by Topalain et al. (*J. Immunol. Meth.* 102:127, 1987). These cells are then infected with the L.hIL-1RSN retroviral vector expressing the human IL-1 receptor. Methods for efficient transduction and selection of TILs in G418 have been previously described (Kasid et al., *Proc. Natl. Acad. Sci. USA* 87:473, 1990). These transduced cells are then amplified in culture and infused into patients as previously described by Rosenberg et al., *N. Engl. J. Med.* 323:570, 1990).

We claim:

1. A method for producing a CD8$^+$ cytotoxic T lymphocyte (CTL) capable of T helper cell ($T_H$)-independent growth comprising introducing into a $T_H$-dependent CD8$^+$ CTL a recombinant expression vector encoding an Interleukin-1 receptor wherein the Interleukin-1 receptor is capable of stable expression and when expressed enhances growth or proliferation of the CTL.

2. A method according to claim 1 wherein the CD8$^+$ CTL is a human CD8$^+$ CTL.

3. A method according to claim 1 wherein the CD8$^+$ CTL exhibits specificity for an antigen.

4. A method according to claim 2 wherein the CD8$^+$ CTL exhibits specificity for an antigen.

5. A method according to claim 3 wherein the antigen is a tumor or viral antigen.

6. A method for producing an antigen-specific CTL capable of T$_H$-independent growth comprising the steps of:
   (a) isolating from an individual exposed to an antigen a sample population of CTL cells cytolytically reactive against cells bearing said antigen; and
   (b) introducing into a subpopulation of the cytolytically reactive CTL cells a recombinant expression vector encoding an Interleukin-1 receptor wherein the Interleukin-1 receptor is capable of stable expression and when expressed enhances growth or proliferation of the CTL.

7. An antigen-specific T$_H$-independent CD8$^+$ CTL comprised of recombinant DNA or RNA encoding an Interleukin-1 receptor wherein T$_H$-independence results from expression of the encoded Interleukin-1 receptor.

8. An antigen-specific CTL produced by the method of claim 1.

9. An antigen-specific CTL produced by the method of claim 2.

10. An antigen-specific CTL produced by the method of claim 3.

11. An antigen-specific CTL produced by the method of claim 4.

12. An antigen-specific CTL produced by the method of claim 5.

13. An antigen-specific CTL produced by the method of claim 6.

* * * * *